United States Patent
Kriger

(10) Patent No.: US 7,803,111 B2
(45) Date of Patent: Sep. 28, 2010

(54) VEHICLE WITH ON-BOARD OVERWEIGHT AND OBESITY PREVENTING SYSTEM AND METHOD

(76) Inventor: Yefim Kriger, 445 Beaver St., # A10, Ansonia, CT (US) 06401

( * ) Notice: Subject to any disclaimer, the term of this patent is extended or adjusted under 35 U.S.C. 154(b) by 58 days.

(21) Appl. No.: 12/315,003

(22) Filed: Nov. 26, 2008

(65) Prior Publication Data

US 2009/0132099 A1    May 21, 2009

Related U.S. Application Data

(62) Division of application No. 10/923,535, filed on Aug. 20, 2004, now Pat. No. 7,465,272.

(60) Provisional application No. 60/545,902, filed on Feb. 12, 2004.

(51) Int. Cl.
A61B 5/00    (2006.01)

(52) U.S. Cl. .................. 600/300; 128/921; 177/25.19

(58) Field of Classification Search .................. 600/300, 600/301; 128/903–905, 920
See application file for complete search history.

(56) References Cited

U.S. PATENT DOCUMENTS 6,425,862 B1 *    7/2002    Brown .................. 600/300

* cited by examiner

*Primary Examiner*—Henry M Johnson, III
*Assistant Examiner*—Kai Rajan
(74) *Attorney, Agent, or Firm*—Robert H. Bachman

(57) ABSTRACT

A motor vehicle and a method of operating same, including an on-board vehicle microcomputer having a memory, and a display connected to the microcomputer. An on-board weighing apparatus located in the vehicle is adapted to weigh a person in the vehicle and provide an input to the on-board vehicle microcomputer of the weight of the person from time to time, whereby a weight trend can be analyzed for the person and overweight or obesity condition of the person that may develop in a short period of time, if any, will be forecasted and information of such weight trends provided to a health care professional to prevent it.

23 Claims, 26 Drawing Sheets

VEHICLE WITH ON-BOARD OVERWEIGHT AND OBESITY PREVENTING SYSTEM AND METHOD

CROSS REFERENCE TO RELATED APPLICATION

This application is a division of co-pending U.S. patent application Ser. No. 10/923,535, filed Aug. 20, 2004, now U.S. Pat. No. 7,465,272, issued Dec. 16, 2008, and is related pursuant to 35 USC 120 to application Ser. No. 10/349,720 filed 23 Jan. 2003 [U.S. Pat. No. 6,816,807 issued Nov. 9, 2004] and to provisional application 60/545,902 of 12 Feb. 2004.

FIELD OF THE INVENTION

The present invention relates to a vehicle having an onboard overweight and obesity preventing method and system that analyzes the weight progress of a person, forecasting obesity conditions that may begin in a short period of time and provides information to the person and to a health care professional to prevent possible overweight and obesity of the person.

BACKGROUND OF THE INVENTION

The problem of overweight and obesity has now become a nation-wide problem for the USA. More than 60% of Americans (about 127 million adults) are overweight (see websites of American Obesity Association www.obesity.org, Centers for Disease Control www.cdc.gov, etc.) and most are car drivers. There are a number of weight control systems and methods to lose weight. Many weight control plans are available to individual users from which the person can select a particular program designed to control the weight of that individual and, associated with such programs are programs involving exercise and like physical activities. Many different kinds of electrical scales have also been suggested for diet and weight control plans. For example, U.S. Pat. No. 4,318,447 entitled "Diet Scale with Weight Progress Indicator" issued to Northcutt in 1982, discloses a diet scale with a digital readout and microcomputer that is used to enable a dieter to enter a diet program having an objective weight and a given time interval. U.S. Pat. No. 4,423,792 entitled "Electronic Scale Apparatus and Method of Controlling Weight" issued to Cowan in 1984, discloses an apparatus that includes electronic circuit in which the weight of the individual at the selected point in time can be compared against the base weight. The U.S. Pat. No. 4,576,244 entitled "Dieter's Weighing Scale" issued to Zeigner et al in 1986, discloses a talking electronic scale with microprocessor that compares the goal weight with the present weight to actuate a voice synthesis device to provide preselected comments appropriate to the comparison. In U.S. Pat. No. 4,577,710 entitled "Apparatus for promoting good health" issued to Ruzumna in 1986, there is disclosed an apparatus that may be embodied in a standard version for providing standard messages based upon departure of measured weight from desired weight of a person. A Closing Size Matrix contains closing size information which is a function of age, size, and weight of a person and may be used to find correct weight. The U.S. Pat. No. 4,844,187 entitled "Future weight machine" issued to Jabero in 1989, discloses an apparatus including means for determining the weight of the individual. The individual may enter the estimated weight of the clothing being worn, or the apparatus may automatically employ a standard correction factor.

Selecting food and counting the consumption of food calories is a common function of many weight control systems. In U.S. Pat. No. 5,412,564 entitled "System and Method for Diet Control"_issued to Ecer in 1995, there is disclosed a diet control system that employs "smart cards" having memory and microprocessor for writing information at a food store or a restaurant check-out counter for collecting electronically the dietary nutritional consumption.

All the above-described patents require the dieter to have the scale on the floor at home and have the same weighing procedure. Thus the dieter has to find time to step up on the scale. As a result, the described patents do not help a dieter who is busy and highly active to choose a diet and lose weight and keep health in good condition. These activities often depend on a mood, physical state, and free time of the individual. As a result, an individual very often does not obey the requirements of the weight loss program and exercise plans on time or does not accomplish them.

The U.S. Pat. No. 6,649,848 entitled "Vehicle with onboard dieters' weight progress identifying and control system and method" issued to Kriger in 2003, discloses an on-board vehicle weight progress control system that weighs the driver's seat when a vehicle gear selector is in the "Park" position and memorizes it's value to calculate the weight of the driver that will be weighed together with the driver seat in the future.

When the driver sits down on a driver seat, he/she is prompted to keep his or her legs out from the floor and away from the pedals, and the system weighs the driver in a few seconds.

By using an on-board vehicle dieter's weight control system each driver and/or passenger in a car could get help to prevent possible overweight. It is the principal object of this patent to extend the utility of a motor vehicle, especially a passenger vehicle such as an automobile, a van, and even a boat, so that the time spent in the vehicle can be utilized more efficiently and the interaction of the vehicle with the driver and/or passenger can be improved.

An automobile equipped with this invention automatically weighs the driver and/or passenger and provide the ability to monitor that weight, manage and control that weight, and provide whatever information may be required for the dieter in that regard. The invention utilizes microcomputer facilities that are enhanced by an ability of dialoging between the on-board microcomputer and the driver and/or passenger. The on-board vehicle weight progress control system manages measurement of the dieter's weight during a time when he or she is in the vehicle seat during a trip and does not waste extra time for this procedure so that one cannot forget about and miss the weight measurement. This patent provides a safety service for the driver-dieter by use of an algorithm of availability during a trip and traffic recognition routine. The on-board system of this patent is thus more reliable than any in-door weight progress control system and method because it helps the dieters to shorten the time and attention of the dieters' activities and also helps to manage their health.

Another reason for a device weighing a person in a vehicle is to use it in a car safety system. For example, in U.S. Pat. No. 5,232,243 entitled "Occupant sensing apparatus" issued to Blackburn et al. in 1993, an occupant sensing apparatus for use in an occupant restraint system comprises a film having an electrical characteristic with changeable states and a contact member. An electrical circuit is connected to the film for providing a signal when an occupant in a car seat. In car safety systems, a sensor is employed to weigh an occupant of a vehicle seat and to control an inflation fluid directed into a restraint accordingly to the weight of the car seat occupant. In U.S. Pat. No. 5,573,269 entitled "Apparatus and method for sensing and restraining an occupant of a vehicle seat" issued to Gentry et al. in 1996, an apparatus for sensing and restraining an occupant of a vehicle seat includes a weight sensor and a seat incline sensor. The weight sensor senses a sensed weight of an occupant The incline sensor senses a characteristic which affects the difference between the sensed weight and the actual weight of the occupant. Another characteristic that affects the difference between sensed weight and real weight of an occupant is a position of occupant's feet on the car floor (a distance between the occupant's feet and a car seat).

Apparatus includes foot sensors for sensing the distance between the occupant's feet and a car seat. The apparatus includes a controller and an inflatable vehicle occupant restraint. The controller determines a computed weight of the occupant as a function of the sensed weight and the both characteristics (the car seat incline and the distance between the occupant's feet and the car seat). Inflation fluid is directed into the restraint to inflate the restaurant and is controlled in response to the computed weight determined by the controller. As a driver weighing device, the system disclosed in U.S. Pat. No. 6,092,838 entitled "System and method for determining the weight of a person in a seat in a vehicle" issued to Walker in 2000, may be used. This system detects the weight of a person seated in a vehicle seat and sends a signal to the air bag actuation controller if the output voltage of the operational amplifier is greater than the predefined level. The other device that may be used for the same purposes is a system disclosed in U.S. Pat. No. 6,069,325 entitled "Seat Weight measuring apparatus" issued to Aoki in 2000, where a seat measuring apparatus measures a seat weight including a weight of a passenger sitting on an automotive seat.

All described above on-board vehicle systems to weigh an individual are not convenient or are not accurate because they use different kinds of indirect methods to weigh the entire body of an individual.

OBJECTS OF THE INVENTION

It is a principal object of present invention to enable, by acquiring and analyzing aggregate information about weight control activities of a dieter in a vehicle, an on-board vehicle overweight preventive system to be correct, friendly, and specific in any recommendation to a dieter in a vehicle, especially a passenger vehicle such as an automobile, a van and even a boat, that may prevent overweight and obesity of the dieter.

It is another object of the invention that an on-board vehicle overweight preventive system, after diagnosing a possible overweight situation in the future, will not give any warning to a dieter immediately but merely suggests that the user begin an exercise and/or diet plan for a calculated trial period and, if the efforts don't result in weight loss, will send a warning to a dieter and to a dieter's primary doctor at the dieter's discretion.

A further object of the invention is to provide an improved method of weighing an individual in a vehicle which avoids drawbacks of earlier methods and which can be practiced more conveniently than earlier methods.

SUMMARY OF THE INVENTION

These objects and others which will become apparent hereinafter are attained, in accordance with the invention, in an automotive vehicle equipped with a driver and passenger weighing apparatus and method to provide an automatic weighing of the driver and/or passenger, and provided with the ability to analyze a weight trend and detect a possible overweight or obesity of a dieter of the vehicle in the future, to assign conditions of a weight loss trial, and provide whatever information may be required for the dieter in that regard. The invention utilizes an on-board vehicle microcomputer facilities enhanced by a touch screen input device which allows dialoging between the on-board microcomputer and the driver and/or passenger.

Prior to the present invention, there was no the on-board vehicle overweight preventive system and method that could detect a possibility of overweight or obesity in the future of an individual in the vehicle and evaluate a period of trial and the other conditions of a weight loss trial plan if an overweight or obese condition is possible and provide whatever information may be required for the dieter in that regard. There was also no convenient and accurate weighing apparatus for weighing a driver-dieter or passenger-dieter in a vehicle that used a direct method of whole body of a dieter in a vehicle measurement.

The present invention provides a self-acquiring on-board vehicle overweight and obese preventive system (SVOPS) and method that makes the on-board vehicle overweight preventive system more correct, convenient, and friendly to an user The present invention helps to prevent future overweight and obesity of a driver and/or passengers in a vehicle by the earliest detection of an overweight or obese condition on a regular, convenient individual basis and evaluation and assigning conditions of a trial weight loss plan. The SVOPS prevents future overweight and obesity by continuous and convenient identification of weight progress and predicting an overweight condition of a driver and/or passengers in a vehicle and by selecting from it's memory lifestyle recommendations, exercises, and, possibly, diets included by permission of the medical and nutrition authorities that are interested in overweight and obese patients in the earliest stages of their illness.

A principal feature of the present invention is to provide an on-board vehicle overweight preventive system to be specific in lifestyle recommendations. For this purpose, the on-board vehicle overweight preventive system acquires measurements of an individual's weight several times during each day and evaluates weight progress made after each intake by each individual that employs the system.

To do this the system creates a of weight progress after intakes that contains pairs of a measured weight of a dieter and time of the measurement. By comparing each of the two sequential weight measurements, the system recognizes time, value, and number of everyday intakes. Certain algorithms in a memory of the system allow the system to create a database of weekday and weekend weight progress after intake patterns of an individual in a vehicle. This allows the system to send more accurate messages and lifestyle recommendations of the medical authority to the dieter.

For example, if the on-board vehicle overweight preventive system finds that everyday food intake is larger at night, it will be able to give a message to a dieter about lifestyle recommendations of medical authority in that regard. An approximate average of everyday dieter's weight measurements in a vehicle may be 2, 4, or 6 times per day. All this means that the vehicle overweight preventive system collects needed data, analyzes this data, and can make a decision. In other words, the system is truly an on-board vehicle self-acquiring overweight preventive system (SVOPS).

Another feature of a system of this invention is that SVOPS, after diagnosing a possible overweight situation in the future, will not give a warning to a dieter immediately after diagnosing a possible overweight. After diagnosing a possible overweight situation that may occur in, say several months, SVOPS may merely suggest that the user begin an exercise program for a trial period (TP) depending on age and an overweight level of a dieter, provide lifestyle recommendations of a medical authority, and positively reinforce healthy weight trends during this TP. If an exercise program doesn't result in weight loss, SVOPS will suggest a more intense exercise program or change a diet and will continue to provide lifestyle recommendations during this new TP and will continue to check weight progress by the use of the algorithms of a Weight Trend Analyzer routine. After this trial period, SVOPS makes a decision and, if the previous efforts didn't result in weight loss, in a very friendly way will tell all about results of the last TP to a dieter and send a message to a dieter's primary doctor at the dieter's discretion.

Another feature of present invention is that SVOPS is a very friendly and confidential in terms of the overweight warning to a dieter. SVOPS will, at a user's discretion, not show warnings of overweight. If during the SVOPS installation (when a dieter is weighing at the first time) a dieter is overweight, SVOPS will show it on a fitness screen only at user's discretion. If the first day using a SVOPS a dieter is not overweight, the system will send a message. If the Weight Trend Analyzer routine discovers that there is an overweight or obesity probability in several months, SVOPS may send a warning message to a dieter's primary doctor at dieter's discretion only.

Another feature of the present invention is that the SVOPS, after diagnosing a possible overweight situation in the future, has some different patterns of weight loss trials that depend on the conditions. There may be a 1 week, 2 week, 1 month, 2 month, 3 month, 6 month, and 1 year trial period, and the goals of a trial may be different. If the result of trial is positive, SVOPS ill encourage the dieter (tell a joke, sing a song, etc.). If a dieter has made progress, a trial may be continued on the same conditions or may be changed. SVOPS may produce a hard copy of a trial result.

If the result of a trial is not good, another trial period may be arranged on the same or the other conditions, and a warning about future overweight, if any, may be sent to a dieter and to the dieter's primary doctor or other health care professional at the dieter's discretion.

A further feature of the present invention is that by using the regular weekday and weekend after-intake patterns created and receiving information from a dialog with a dieter or from a GPS (Global Positioning System), SVOPS determines the name of a place (McDonalds, Pizza Hut, etc.) where the dieter eats.

Another feature of the present invention is that the menus most popular and most used restaurants and buffets (McDonalds, Pizza Hut, Subway, D'Anjello, etc.) with the names of the basic dishes and number of calories, fat, cholesterol, etc. in each of them are included into Menus Database of the SVOPS.

Another feature-of the present invention is that after SVOPS recognizes a dieter's schedule of an everyday intake and discovers when and where he/she eats, SVOPS suggests to a dieter what food to eat and how much.

Another feature of the present invention is that all recommendations of the best nutrition, dietetic, health, etc. companies and the best medical authority are included into the SVOPS's algorithms and messages.

Another feature of the present invention is that during installation of the SVOPS, a dieter may choose a feature indicating time (morning, day, evening) and day of week when he/she prefers to get an overweight warning.

Another feature of the present invention is that SVOPS gives a warning when an individual has an Extreme Weight Loss. It makes SVOPS more universal. When an individual is not overweight and continuously loses weight and his/her weight goes down to a certain level, SVOPS continues to monitor weight of an individual during a certain trial period. If an individual continues to lose weight, the system sends a warning to the primary doctor of the individual at the individual's discretion.

Another feature of present invention is that to get more flexibility SVOPS is realized as a Hybrid Overweight Preventive System (HOPS) that consists of two parts:

a. A vehicle part that is a SVOPS which may have all the functions described or restricted functions, for example, to work only as a weight progress data collector and analyzer.

b. A home part that is a SVOPS installed at home which doesn't have the functions of weight progress data collecting and analyzing but may be used to read medical information concerning lifestyle recommendations, diets, etc.

Another feature of present invention is that to make SVOPS have the ability to receive any data from or transmit any data to any sources outside a vehicle, to input a new data to the databases of the SVOPS and to get for an individual new recommendations and entertainment data, a floppy disk, CD, and/or rewritable CD drives are included into a SVOPS as options.

Another feature of the present invention is:

a) to use SVOPS by scientists and doctors to analyze a correlation of the weight progress graph of an individual and possible illness in order to define or predict a certain kind of illness, and b). to get global statistics from a certain part of the population about the possible correlation between the weight progress graph and illnesses in order to show certain patterns for use in practice.

Another feature of the present invention is to keep or remove a personal data of an individual in case of selling a car or buying a new one. A Vehicle Change (VC) feature is included for these purposes in the SVOPS. In case of selling a car, owner of a car uses a VC feature to save all his/her data as a user of the SVOPS and carry this data, probably, to a SVOPS on another car. For this purpose, the owner of the car goes to VC menu and copies his/her private data to a floppy disk or rewritable CD and uninstalls the SVOPS. In case a new SVOPS is installed on a buyer's car, a new owner may copy his/her private data to the new SVOPS.

Another feature of the present invention is that to realize a drive safety routine, a speed sensor of the car is included into the SVOPS. The sensor is connected to the microcomputer of the SVOPS through a conditioning circuit, sample and hold circuit, Analog-to-Digital Converter (ADC), and buffer. In case, a signal of the car's speed is received from a speedometer that exists in another system of the vehicle, this signal has to be connected to the microcomputer of the SVOPS through a conditioning circuit, sample and hold circuit, ADC, and buffer. Another feature of the present invention is that to make SVOPS usable for children more than one year old (those whose appointments for the pediatrician are not as frequent as for toddlers), an electrical scale and height meter are mounted in a children's car seat and connected to the microcomputer.

Many people travel much by the car. They are often on a business trip or are driving during holidays, vacations, or weekends together with their children. The number of miles an American drives has doubled since 1963 and the number of overweight children between 6 and 11 has doubled since 1973 (see "America is driving itself into obesity" by Ellen Goodman, The Advocate, Feb. 9, 2004, Southern Connecticut Newspapers, Inc.) To predict overweight of children, it is necessary to start to use SVOPS as soon as possible and when a child is not older than 1-2 years. To predict overweight of such children correctly, it is necessary to input into SVOPS database all data about weight and height that the primary pediatrician has gotten before the SVOPS has started to monitor weight progress of a child. For this purpose SVOPS has a procedure of inputting into it's database a classified file prepared by pediatrician responsible for this information. The file signed by the pediatrician is prepared on a floppy disk or by the use the other media compatible with the microcomputer and includes a child's portfolio and all data (weight, height, time, etc.) that will build a weight progress data of the child for a certain period of time in the SVOPS's database. Starting with 2-4 year old children, when parents have appointments with a pediatrician seldomly, SVOPS measures the weight of a child by a dialoging with the child directly and sings a song as encouragement. A parent may measure a height of a child by the use of special markers on a rear seat of a car and insert this data in a system. Parents may also use a supplemental cushion for car rear seats with the marks on it to measure height of the children by laying a child on the rear car seat and measuring one's length.

Another feature of the present invention is that to serve a pregnant woman, she is questioned "Are you pregnant?" during a SVOPS Introduction routine if an answer on a "Sex" or gender question is "Female." The special data for pregnant women included into databases, and Pregnant Woman routine is used.

Another feature of the present invention is that a Dialogue database included into SVOPS that consists of all questions and messages of dialogues between SVOPS and an individual Another feature of the present invention is that because of difficulties in weighing a sitting individual in a vehicle, a special weighing apparatus and methods of weighing an individual in a vehicle are provided. One weighing device of this type of weighing apparatus is located in a car seat of an individual in a vehicle. Additional weighing device of the weighing apparatus for the foot part of said individual body weighing is fixed or retractable from a suitable part of the vehicle or located in a floor mat. Each device weighs a part of a whole individual's weight.

Another feature of the present invention is that height measurements for any age children may be done by using a tape marked in centimeters or inches that is located in a pocket in left rear door above a left rear seat of a car. A tape has a spring and may be removed from the pocket for the length of a child. A measured length of the child, lying on the left rear car seat, may be inputted into the microcomputer manually.

Another feature of the present invention is that SVOPS may be manufactured as a separate, stand alone system, independent from the type of the vehicle or as a part of the vehicle depending on the type of a vehicle.

Another feature of the present invention is that to make the use of SVOPS more exact, each individual, especially a sportsman, will be asked to input a body fat coefficient. Each woman will be asked about pregnancy. SVOPS will use a separate database for pregnant women. Each individual will be asked about the presence or absence of a chronic disease.

Another feature of the present invention is that the SVOPS has three modes of operation:

1. SVOPS is turned on after an operator of a vehicle activates a keyless open door device. SVOPS continues to be in this condition any time during a trip until driver will turn it off.

2. Driver weighing apparatus is activated only if the gear selector in a parking position.

Passenger weighing apparatus is activated at any time when SVOPS is turned on.

3. A screen of SVOPS may be activated if a gear selector is in a parking position or a vehicle is in a heavy traffic with a speed not greater than a certain level. The screen of a passenger Activities controller may be activated any time if the microcomputer doesn't serve a driver.

Another feature of the present invention is that some body parameters, for example, BMI, body fat, etc. are inserted in SVOPS and their values may be changed and used as needed according to modern medical research.

Another feature of the present invention is that a list with main lifestyle recommendations created by medical authorities is inserted into SVOPS to help people to maintain their health.

Another feature of the present invention is that starting at age of 2-4 year old, SVOPS measures the weight of child by a dialoging with one directly and sings a song as an encouragement. A parent may measure a height of a child by the use of special markers on a rear seat of a car and insert this data in a system. Parents may also use a supplemental cushion for car rear seats with the marks on it to measure height of the children by laying a child on the rear car seat and measuring one's length.

When a passenger is a child or teenager (from 2 to 17), SVOPS will ask a driver about their relationship. When weight progress of a child or teenager is not normal, SVOPS will send a message to a driver and/or to a child's primary doctor at driver's discretion.

Another feature of the present invention is that to improve an ability of the SVOPS to identify weight of an individual in a vehicle, a temperature sensor is included into the system.

Another feature of the present invention provides an accuracy of weighing an individual in a vehicle. To prevent an individual's back from touching the seat back during weighing an individual by SVOPS, the initial position of a back of a car seat is the most declined position.

After SVOPS weighs an individual in a car seat (driver and/or a front passenger), an individual may adjust position of a back of a car seat for his/her best convenient. After individual leaves a car, a car seat memorizes the last position of a car seat back and put a car seat back in the most declined position and keeps this position of a car seat back till an occupant of a car seat will return back and will be weighed. After SVOPS weighs the car seat occupant, a car seat back returns to the last memorized position automatically.

The system of the invention is friendly to any human being individual or group of people restricted in a vehicle or in any other moving facility and gets it's inputs and reactions by a voiced dialoging with the system. The system thus may be described as a friendly self-acquiring on-board vehicle overweight preventive system (SVOPS), or psychologically friendly system, or friendly drive helping system, etc. The specific feature of such a friendly self-acquiring system is that it tries to help in a friendly way and improve a spiritual condition of a human being by a voiced dialoging.

The weighing apparatus (WAPP) can employ two weighing methods for weighing an individual in a vehicle. First of all, the WAPP can use at least two weighing devices for weighing an individual in the vehicle. In a basic structure of the WAPP, the first weighing device is located in an individual's car seat and measures a weight of a portion of the individual's body located in the car seat. The weighing platform of the additional weighing device of the WAPP for the foot part of said individual body weighing is fixed or retractable from a suitable part of the vehicle or located in a floor mat and measures a weight of the remainder of the individual's body. An electrical circuit sums up and converts the resulting signal.

This method of weighing an individual in a vehicle differs from prior art in U.S. Pat. No. 6,649,848 entitled "Vehicle with on-board dieters' weight progress identifying and control system and method" issued to Kriger in 2003, in which an accurate method of weighing an individual in a vehicle by lifting up his/her feet was disclosed. Lifting up the feet may not be habitual for some people in a car. The weighing apparatus (WAPP) of present invention has a weighing procedure that is close to the natural position of a sitting driver or passenger in a vehicle especially for women with long legs.

The WAPP uses a transposition weighing method (TP-method) for precise weighing of an individual in a vehicle.

According to the TP-method, the WAPP may define a correct individual's weight by an analyzing a graph of weights of an individual acquired during a period of time from a moment when an individual sits down in a car seat to a moment of time when a signal that a seat belt is buckled appears.

The following weighing procedure (instruction set) is provided for weighing an individual in a vehicle:
1. When you sit down in the car seat, put your feet on a weighing platform near your feet,
2. Keep your hands on your knees (don't touch anything in the car by hand) and don't push a seat back against your back for few seconds,
3. Buckle the seat belt.

This sequence of steps is natural for an individual in a vehicle, but before a start and during the procedure an activated transparent or voiced announcement about this procedure may be used just in case.

In the new type of weighing apparatus, one weighing platform weighs one part a body of an individual. Another weighing platform of the weighing apparatus measures the weight of the rest (e.g. the feet part) of an individual. An electrical circuit is provided for summing up and perhaps converting the resulting signal. Each weighing platform gives an electrical signal. The sum of these two signals is directly proportionate to the weight of the individual and is connected to a conditional circuit. The output electrical signal of the conditional circuit is connected to a microcomputer through an analog to digital converter (ADC) and a buffer.

There has to be a prompt to an individual to put his or her feet on the platform of an additional weighing device so that the individual does not touch anything by hand in a car except to buckle the seat belt.

To weigh a sitting driver or a passenger in a vehicle, one weighing platform of the weighing apparatus is located in a car seat of an individual. Another part of the weighing apparatus may be located:
a). to weigh a driver:
 1). in an additional weighing device that is fixed or Retractable from a suitable part of the vehicle or located in a floor mat under the feet of a driver
 2). in an additional weighing device that is fixed on a gas pedal.
b) to weigh a front passenger: in an additional weighing device that is fixed or retractable from a suitable part of the vehicle or located in a floor mat.

According to the transposition method {TP-method} of weighing a driver in a vehicle it is necessary to begin to weigh a driver at the time when a prompt appears on a dashboard, and a driver puts his or her feet on a weighing platform that is fixed or retractable from a suitable part of the vehicle or located in a floor mat and to finish weighing at time when a signal appears that seat belt is buckled. The weight of a driver measured just at this period of time is more accurate because a driver, probably, doesn't touch the steering wheel or anything else in a vehicle by hand.

It is another object of the invention is to provide an easy method to define a position of the front passenger {facing front} in a car seat of the running vehicle, especially for children that employs an air bag safety system, by using an additional passenger weighing device that is fixed or retractable from a suitable part of the vehicle or located in a floor mat of the car.

It is another object of the invention to provide use of the second additional weighing device in a weighing apparatus to eliminate a possible error by touching anything in a car by driver's or passenger's hand.

This second additional weighing device may be embedded in or mounted above a steering wheel for a driver being weighed.

A driver may be weighed when a car is running by the use of two additional weighing devices. One of these additional weighing devices is fixed or retractable from a suitable part of the vehicle or located in a floor mat. The second additional weighing device is fixed on the gas pedal. In this case the driver's right foot will push the gas pedal via the second additional weighing device. The left foot of the driver has to be on the first additional weighing device.

BRIEF DESCRIPTION OF THE DRAWING

The above and other objects, features, and advantages will become more readily apparent from the following description, reference being made to the accompanying drawing in which.

DETAILED DESCRIPTION OF THE DRAWINGS

Figure 1:
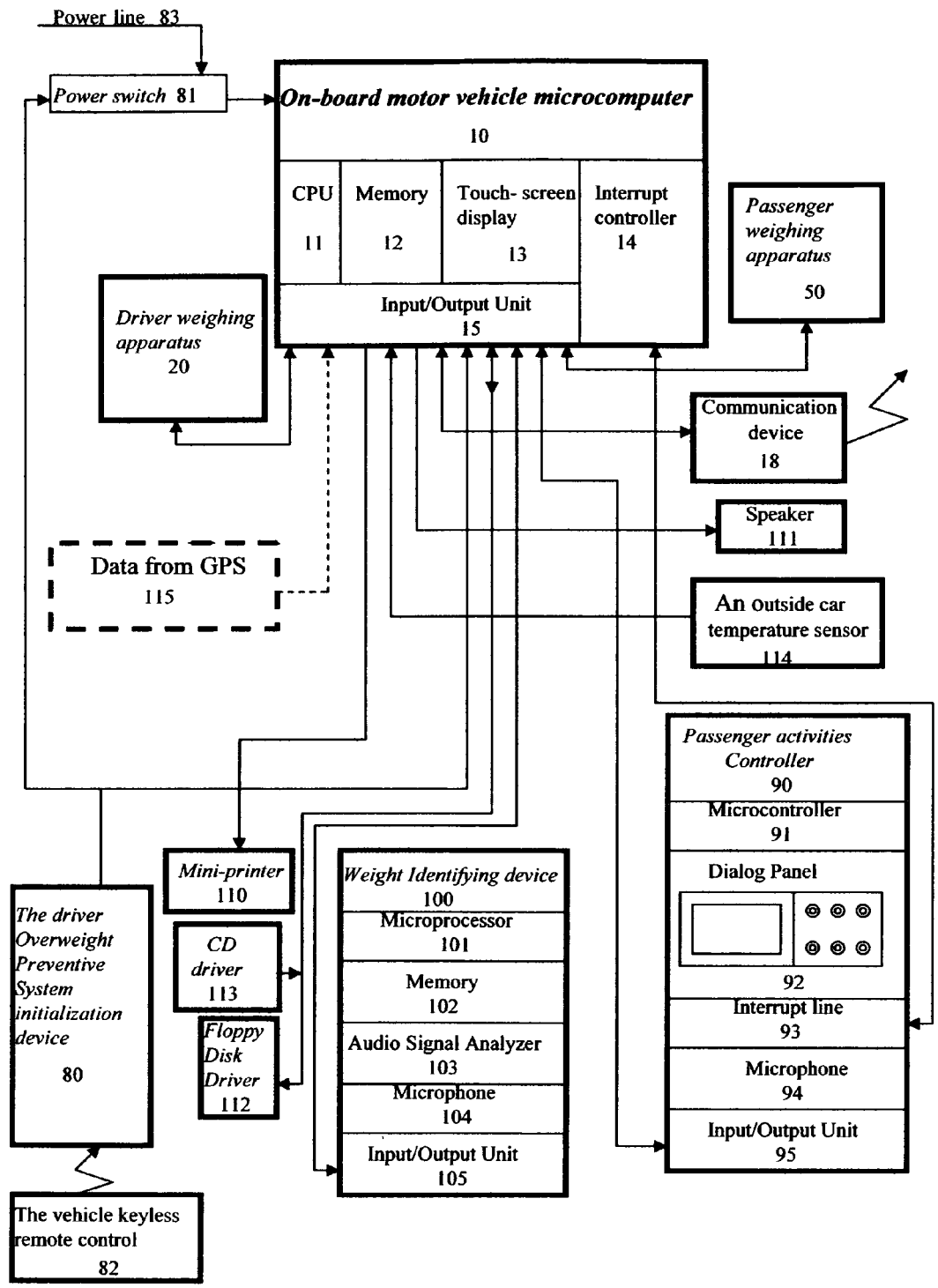
FIG. 1 is a block diagram of the devices that comprise the self-acquiring on-board vehicle overweight preventive system.

FIG. 1 is a block diagram of the on-board motor vehicle self-acquiring overweight preventive system (SVOPS). The system consists of six main devices: on-board motor vehicle microcomputer 10, driver weighing apparatus 20, passenger weighing apparatus 50, the driver overweight preventive system initialization device 80, passenger activities controller 90, and weight identifying device 100. Central processing unit (CPU) 11 of the microcomputer 10 controls all devices of the system by use of a memory 12 and corresponding interfaces that are provided by the input/output unit 15. This description assumes the use of a touch-screen type of a display-input unit 13. An interrupt controller 14 provides monitoring of the passenger weight control activities.

The touch-screen display can be so positioned that it is not visible to passengers and, as will be apparent hereinafter, can be one of a number of such screens positioned so that they can be displayed and be engaged by the passengers. Other kinds of inputs and outputs can be provided, of course, although they are less convenient. Voice operated systems may also be used and a wired or wireless connection can be available to allow a laptop or palm unit to be connected to the microcomputer for transfer of data therebetween.

Figure 3:
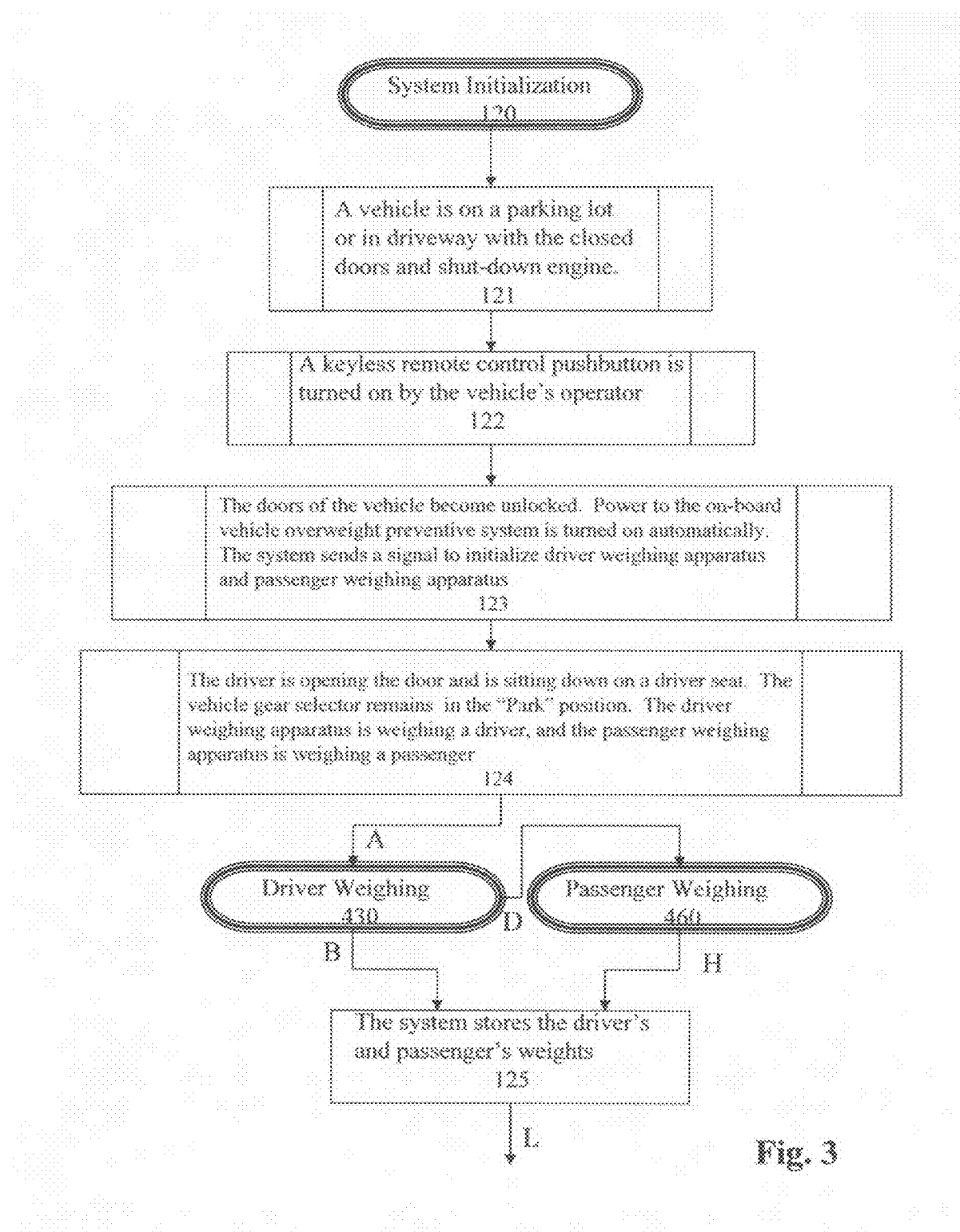
FIG. 3 is a flowchart for the System Initialization routine.

The system starts to work as the vehicle's operator pushes a button of the vehicle keyless remote control 82 outside of the vehicle. At that moment, the driver overweight preventive system initialization device 80 sends an initialization signal to both switch 81 of the power line 83 and the input/output unit 15 of the microcomputer 10. Microcomputer 10 starts its System Initialization routine 120 from step 123 (FIG. 3). Microcomputer 10 controls the power line and "zero" adjustment of both a driver weighing apparatus and a passenger weighing apparatus. A more detailed description of the software routines to serve a driver or passenger as a dieter is given below.

Figure 11:
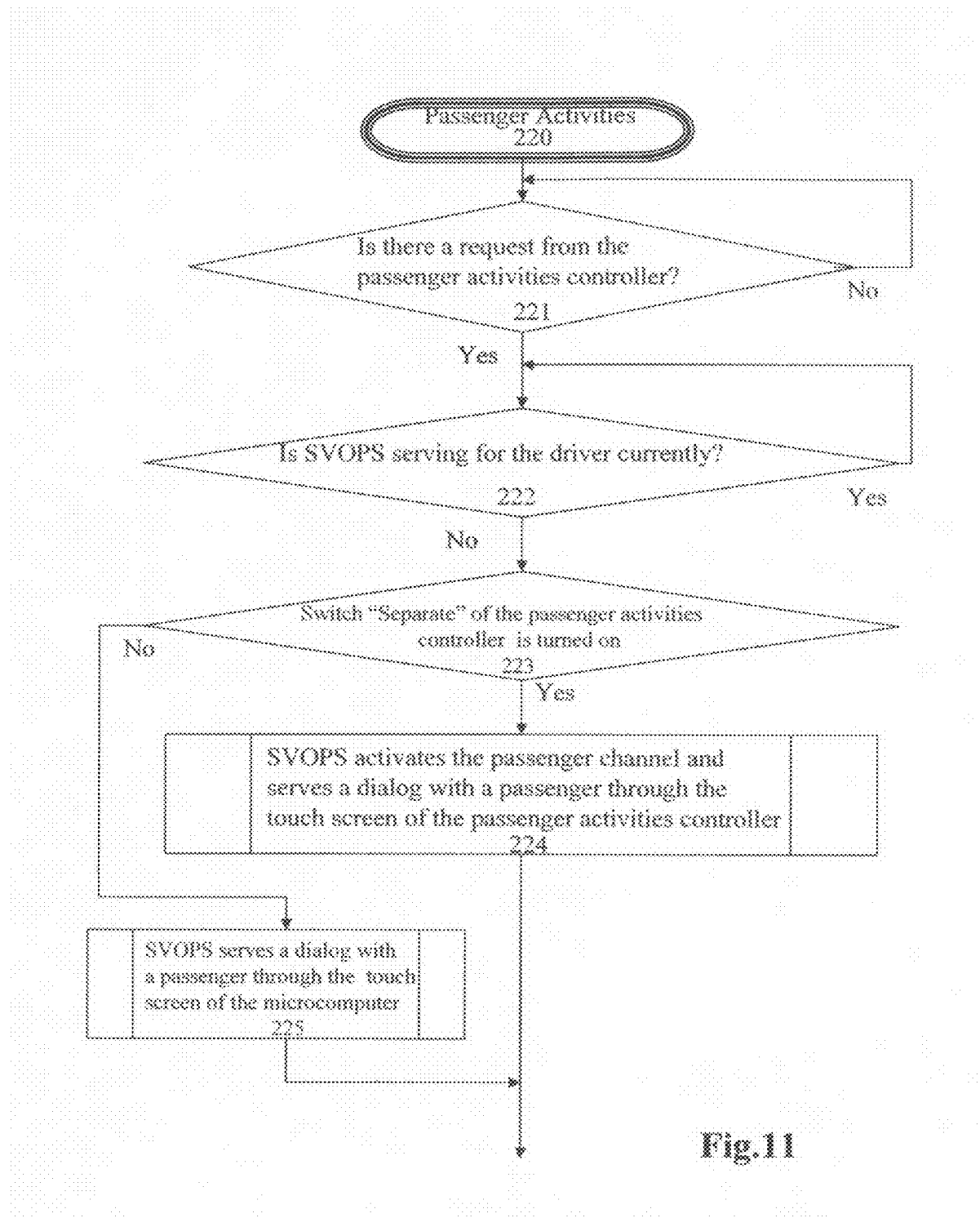
FIG. 11 is a flowchart for the Passenger Weight Control Activities routine.

Passenger activities controller 90 is destined to serve a passenger as a dieter. Passenger activities controller 90 includes a microcontroller 91 that provides all control and processing operations by use of its own memory, dialog panel 92 with touch-screen and push buttons, and microphone 94 to serve a voiced dialogue between a passenger and SVOPS. Input/output unit 95 provides an interface with the microcomputer 10. The passenger starts the Passenger Activities routine 220 (FIG. 11) of the microcomputer 10 by pushing a button or touching a screen area that activates an interrupt line 93 that is connected to the interrupt controller 14 of the microcomputer 10. Microcomputer 10 controls the power line and "zero" adjustment of the passenger weighing apparatus. When microcomputer 10 starts to run the Passenger Activities routine 220, the passenger activities controller 90 makes the interrupt line 93 passive. A more detailed description of the software routines to serve a passenger as a dieter is given below.

Figure 6:
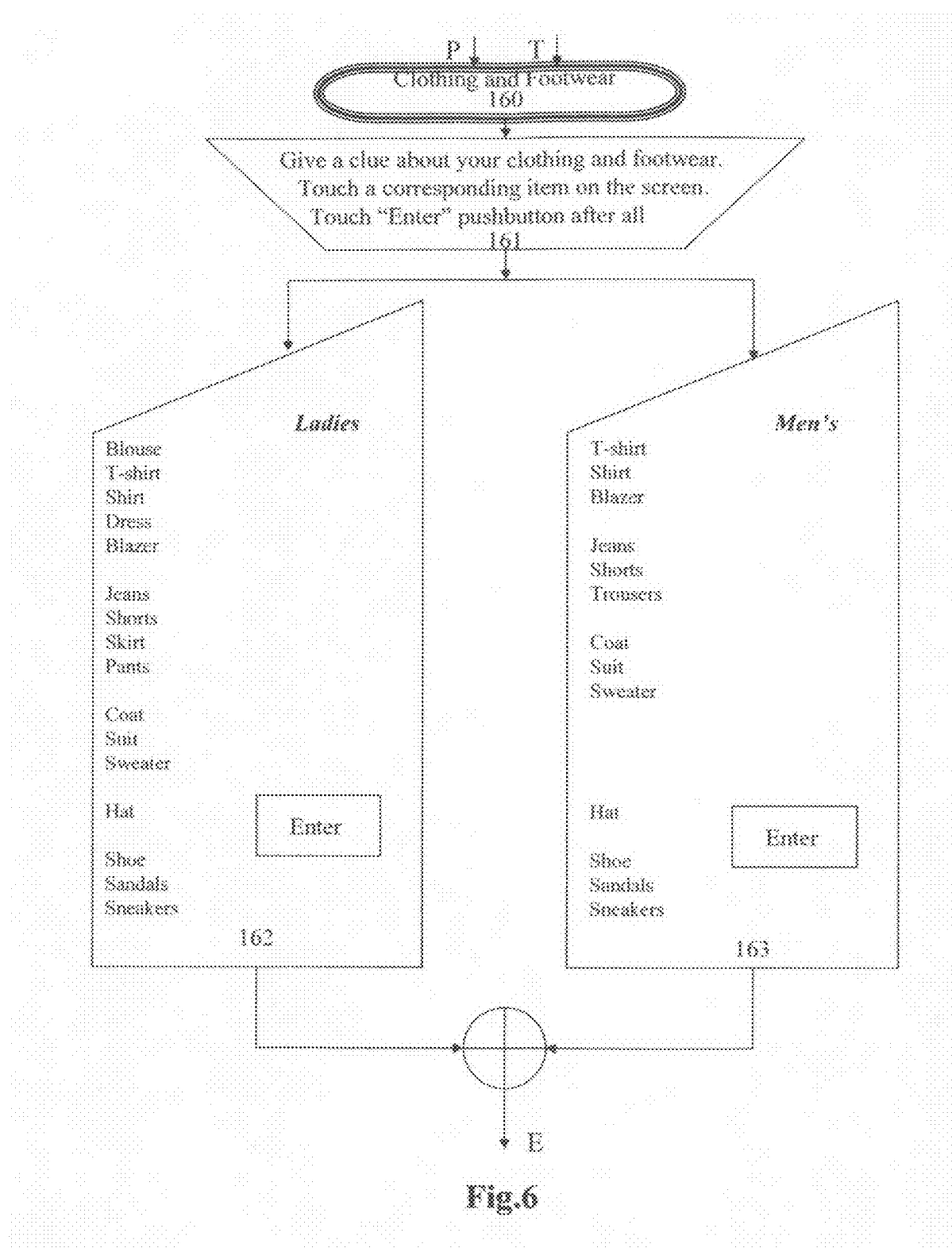
FIG. 6 is a flowchart for the Clothing and Footwear routine.
Figure 7:
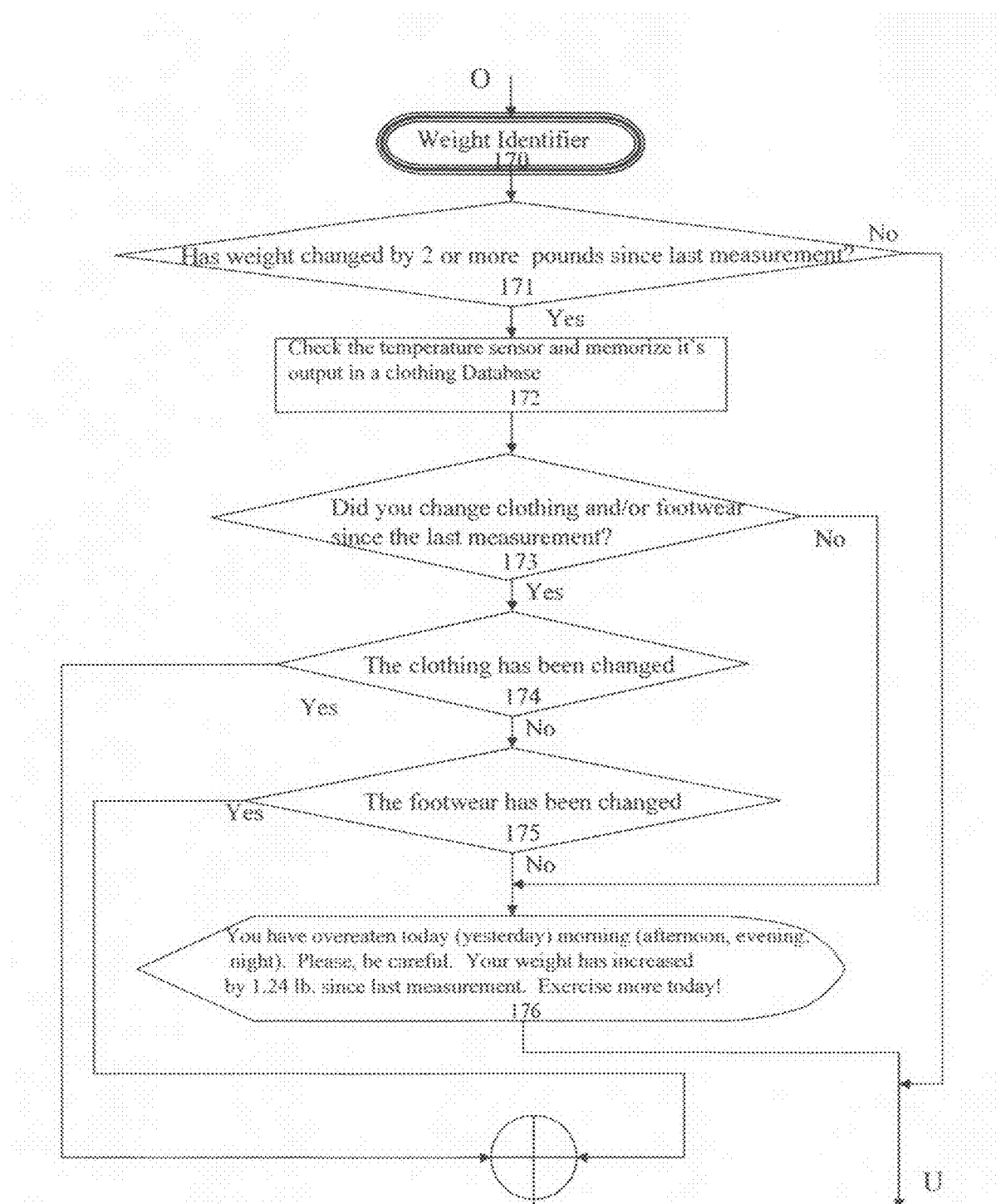
FIG. 7 is a flowchart for the Weight Identifier routine.

The weight identifying device 100 consists of microprocessor 101 and memory 102 that provide resources for recognizing the audio signals by use of an audio signal analyzer 103. The input/output unit 105 provides an interface to the microcomputer 10. There are three peripheral devices included into the system. Mini-printer 110 responds to the Shopping List routine 190 (FIG. 9) to print a weekly shopping list out. Drivers for floppy disk 112 and CD 113 are employed to input to and save data from the on-board motor vehicle self-acquiring overweight preventive system. The on-board vehicle overweight preventive system is distinguished from weight control systems in part by recognizing different clothing and footwear of the driver and/or passenger at the moment of the different measurements of their weights during the current day or during several consecutive days. There are two software routines that decrease any errors because of different clothing and footwear at the different weight measurements: Clothing and Footwear routine 160 (FIG. 6) and Weight Identifier routine 170 (FIG. 7). During the execution of these two routines there is a dialogue between an on-board vehicle overweight preventive system and driver and/or passenger that recognizes any changes in the clothing and/or footwear at the time between the two consecutive weight measurements. It is necessary to realize what clothing and/or footwear have been changed, if any, to decrease the error in the weight measurement. The weight identifying device 100, microphones 94 and 104 incorporated into the passenger activities controller 90 and weight identifying device 100 accordingly, and speaker 111 enable the dialogues between SVOPS and driver or passenger. The driver or passenger can answer just "yes" or "no" during these audio dialogues without touching the touch screen. An audio dialogue makes the driver and passenger feel more comfortable.

To make an on-board vehicle self-acquiring overweight preventive system able to recognize a reason for the unusual large change of a dieter's weight in a vehicle between two consecutive weight measurements, an outside vehicle temperature sensor 114 is included into SVOPS. This will improve the correctness of SVOPS everyday intake patterns and, as result, the lifestyle recommendations to a dieter. Data from a global positioning system (GPS) 115 may also be used.

Figure 2:
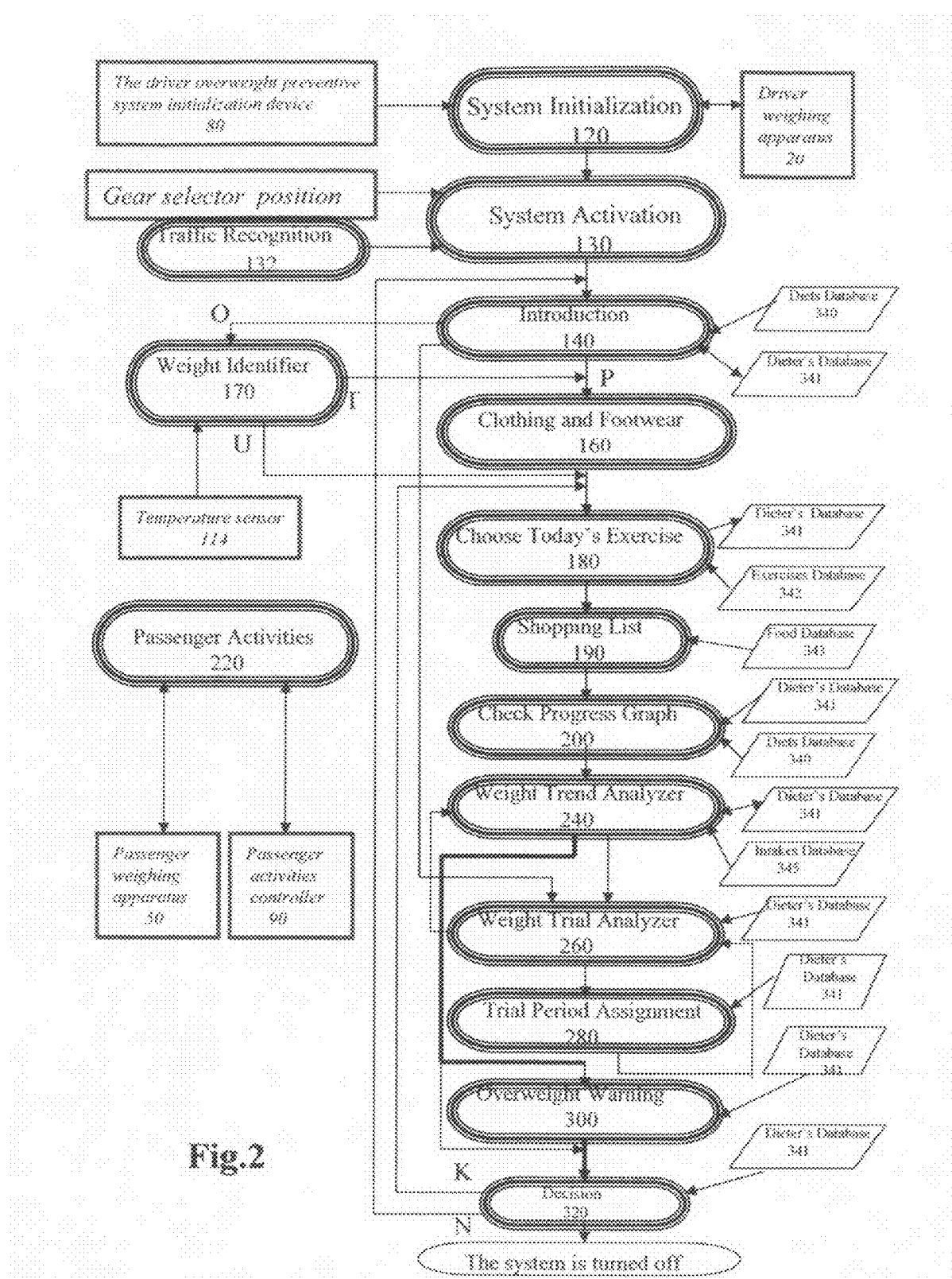
FIG. 2 is a block diagram of the interconnection of the software routines with the hardware and databases.
Figure 4:
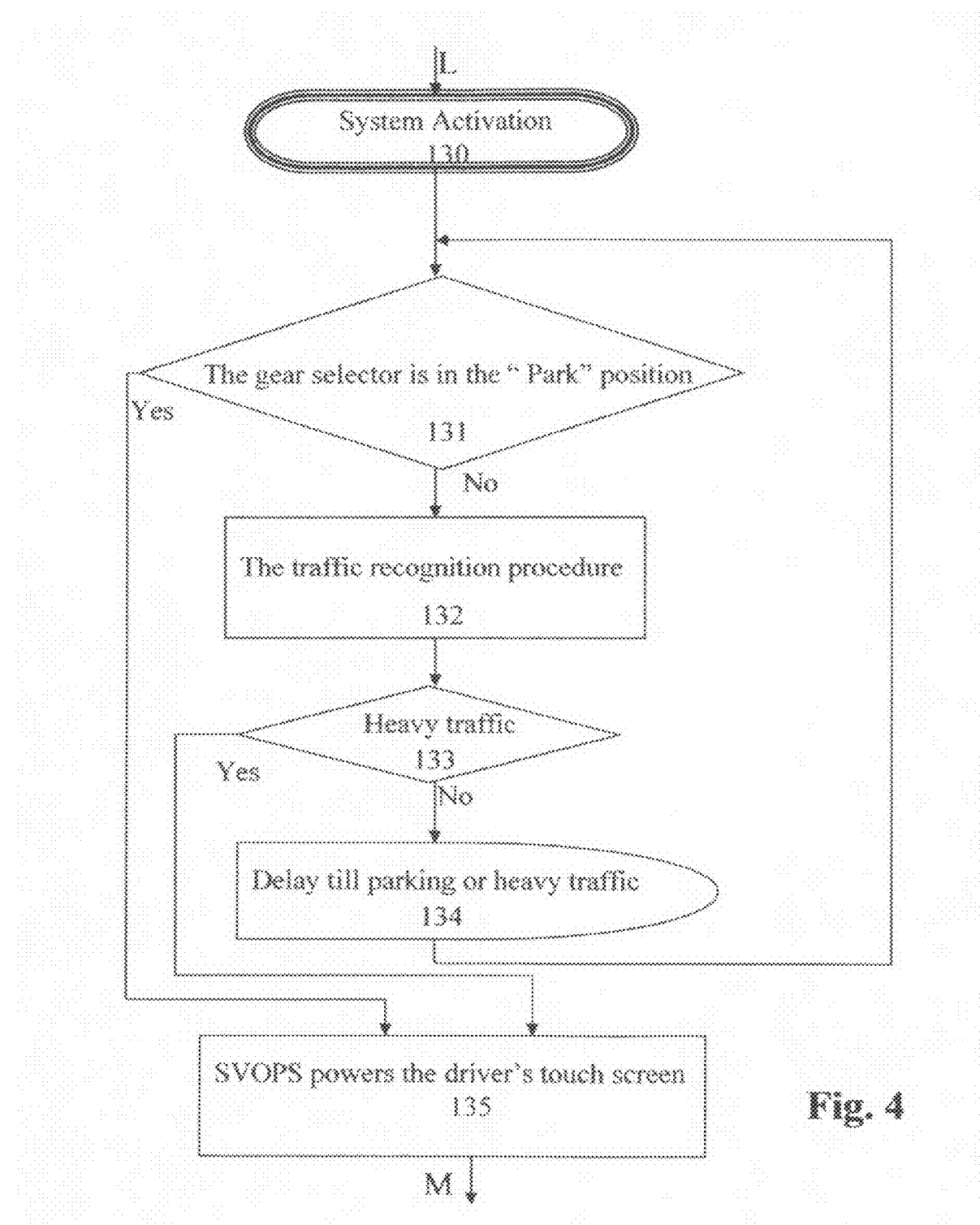
FIG. 4 is a flowchart for the System Activation routine.

FIG. 2 is a block diagram relating the software routines to the units of the on-board motor vehicle overweight preventive system. When the vehicle's operator pushes a button of the vehicle keyless remote control outside of the vehicle, the driver overweight preventive system initialization device 80 sends an initialization signal to the microcomputer 10 that starts its System Initialization routine 120 (FIG. 3), which controls the power of the driver weighing apparatus 20 and passenger weighing apparatus 50. When the driver sits down on the driver car seat, the driver weighing apparatus 20 measures his/her weight, and the System Activation routine 130 (FIG. 4) starts and defines whether the system may be activated because the vehicle is in a safe driving mode. This routine gets information from gear selector position (when the selector is in the Park position) and from the Traffic Recognition procedure 132 (when there is heavy traffic). When a passenger sits down on the passenger car seat, the passenger weighing apparatus measures his/her weight. More detailed descriptions of the driver and passenger weighing apparatus, methods and procedures used for the driver and passenger weighing are given below. If the system is activated, the Introduction routine 140 (FIG. 5) starts. The driver or passenger inputs his/her name and password into the system. If a driver or passenger is a new user, he/she gets recommendations from the "Fitness status" screen 145 and chooses a diet plan from the plurality of diet plans that are in the Diets Database 340 (FIG. 2). The personal driver or passenger data will be memorized in the Dieter's Database 341 (FIG. 2). A Clothing and Footwear 160 (FIG. 6) routine then starts. If the driver or passenger is not a new user, a Weight Identifier routine 170 (FIG. 7) starts. The system recognizes if the weight difference between two consecutive measurements is more than 5 pounds. If any, the system defines the reason for this change of the user's weight by the dialog between system and user. Of course, one skilled in the art can determine that other weight ranges can be programmed into the unit. If the weight has changed because of the clothing or footwear change, the Clothing and Footwear routine 160 starts. This routine memorizes the clothing and footwear of the new user and recognizes and memorizes any changes in clothing and/or footwear if any by the dialog with the user.

Figure 8:
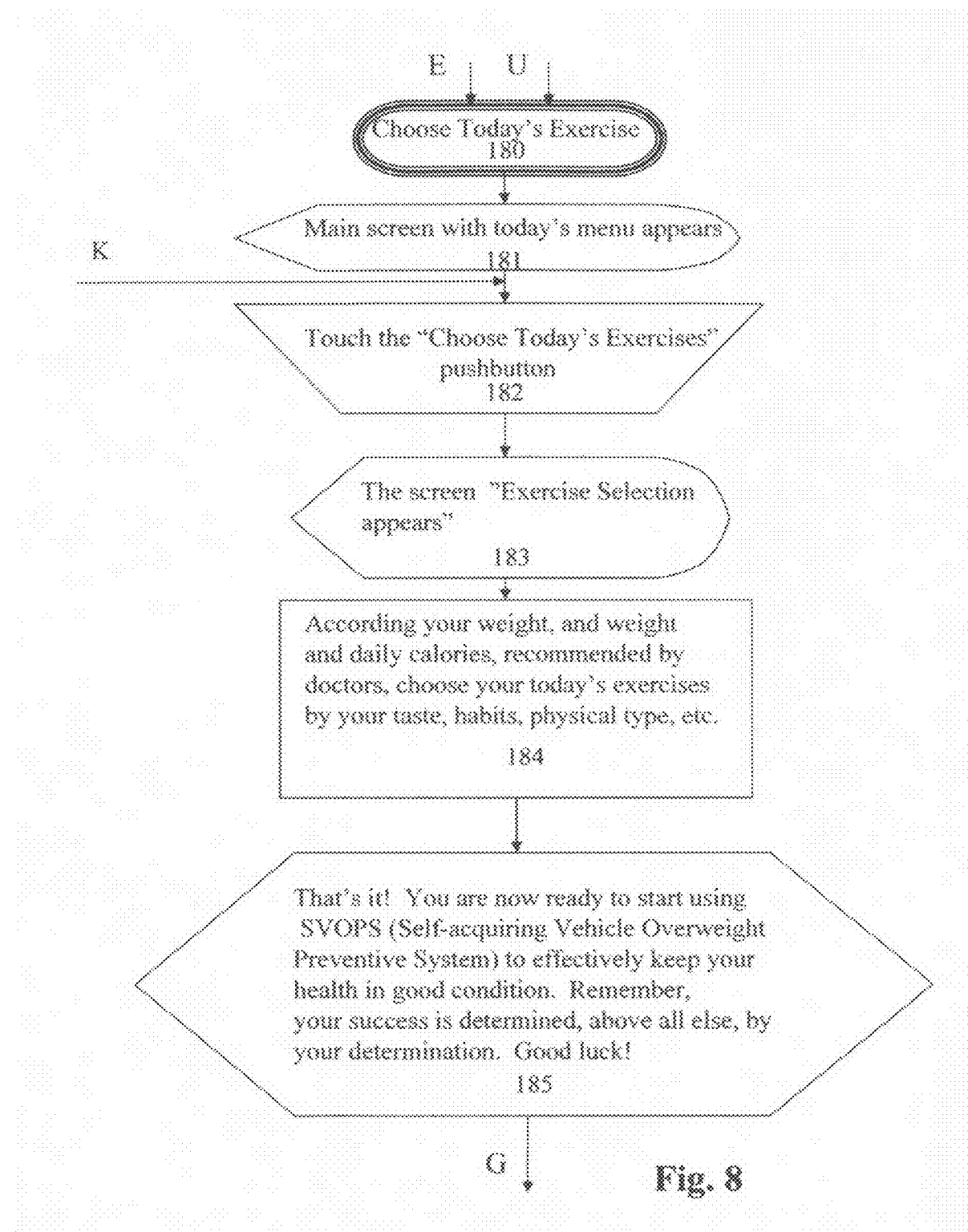
FIG. 8 is a flowchart for the Choose Today's Exercise routine.

In Choose Today's Exercise routine 180 (FIG. 8) the person uses the value of his/her extra pounds or calories to be burned calculated by the system to choose today's exercises from the Exercise Database 342 (FIG. 2). The system memorizes this data in the Dieter's Database. The Shopping List routine 190 (FIG. 9) gives an opportunity to save or print the weekly shopping list for the person by use of the Food Database 343. The person can analyze the result of use of the chosen diet plan by the Check Progress Graph routine 200 (FIG. 10) that employs the Diets Database 340 and Dieter's Database 341.

The Passenger Activities routine 220 (FIG. 11) starts when the passenger activates the interrupt line 93 of the passenger activities controller 90. If the system is not busy (not in use by the driver), it activates a passenger dialog panel 92 and touch screen on it and serves the dialog with the passenger through the passenger activities controller 90. If the switch "separate" on a passenger dialog panel is turned off, the dialog between the person and system will go through the touch screen of the on-board vehicle microcomputer display. In this case, the touch screen of the passenger activities controller will be deactivated.

Figure 12:
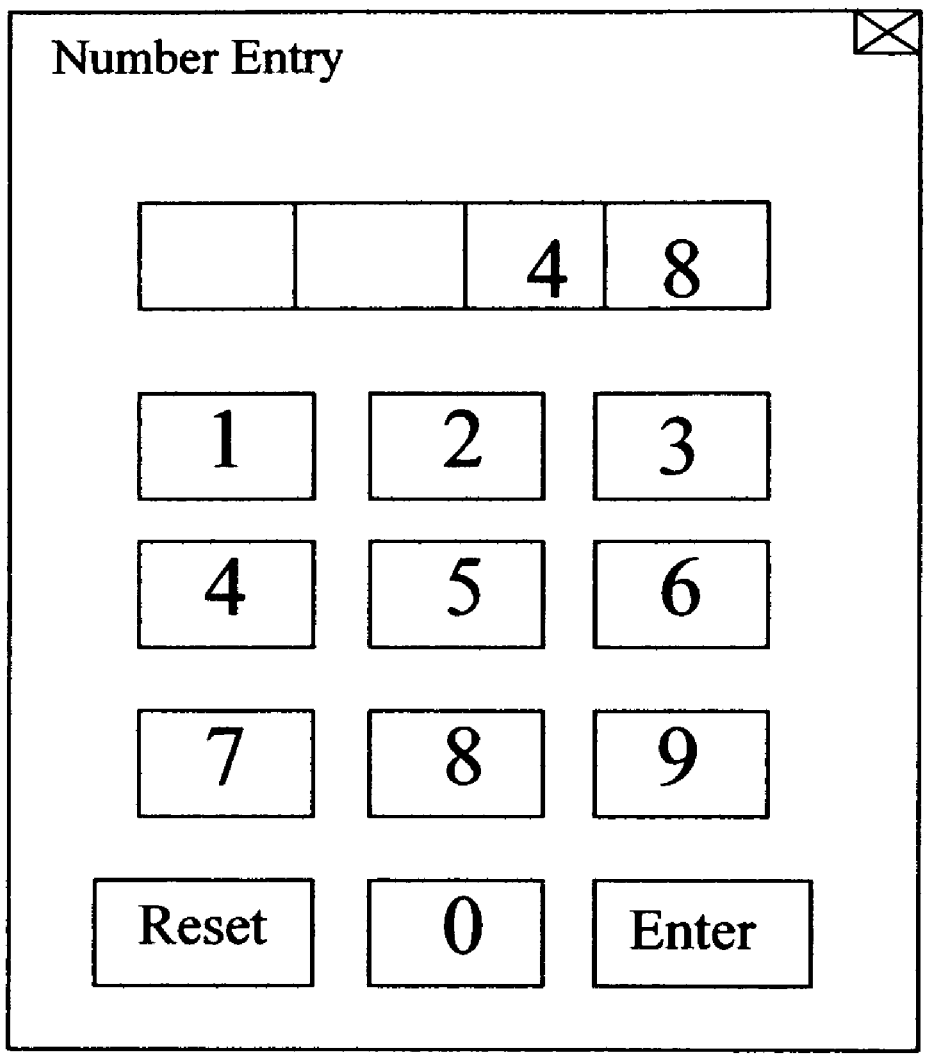
FIG. 12 is a display of the Number Entry pop-up window.
Figure 13:
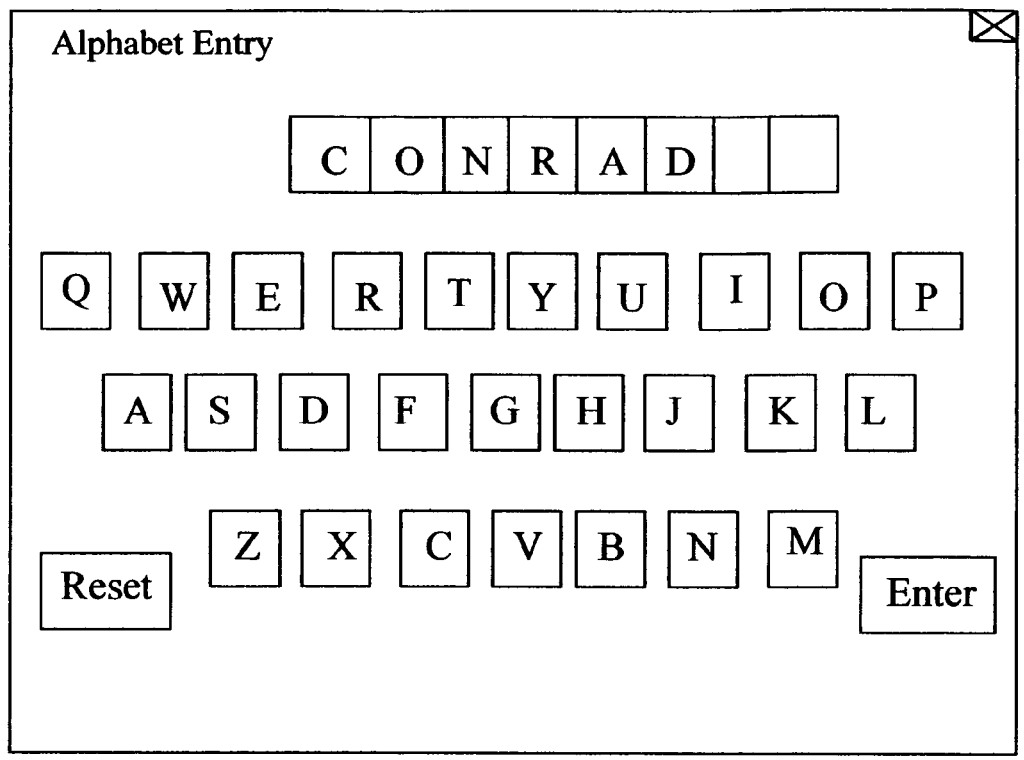
FIG. 13 is a display of the Alphabet Entry pop-up window.

FIG. 12 and FIG. 13 shows a Number Entry and Alphabet Entry pop-up windows. A person uses these two windows for a dialogue between a person and SVOPS to input his/her name, password, and other data into SVOPS during Introduction routine 140.

Figure 14:
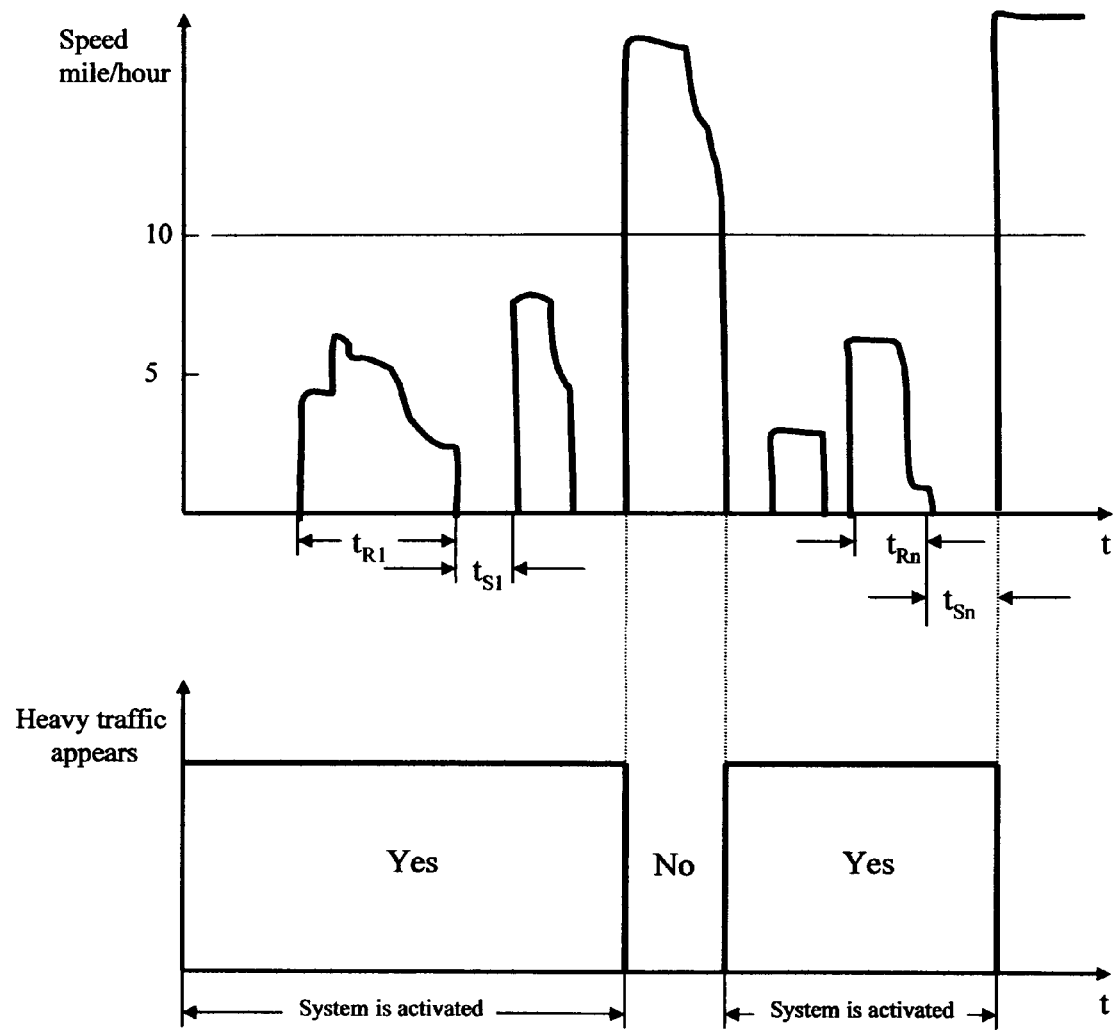
FIG. 14 is a hard traffic recognition procedure.

FIG. 14 shows a chart for the heavy traffic recognition. The "heavy traffic" condition of driving is a state in which the speed of the vehicle is not higher than a certain value. In this case the driver can have a dialog with the system and pay enough attention to driving.

Figure 15:
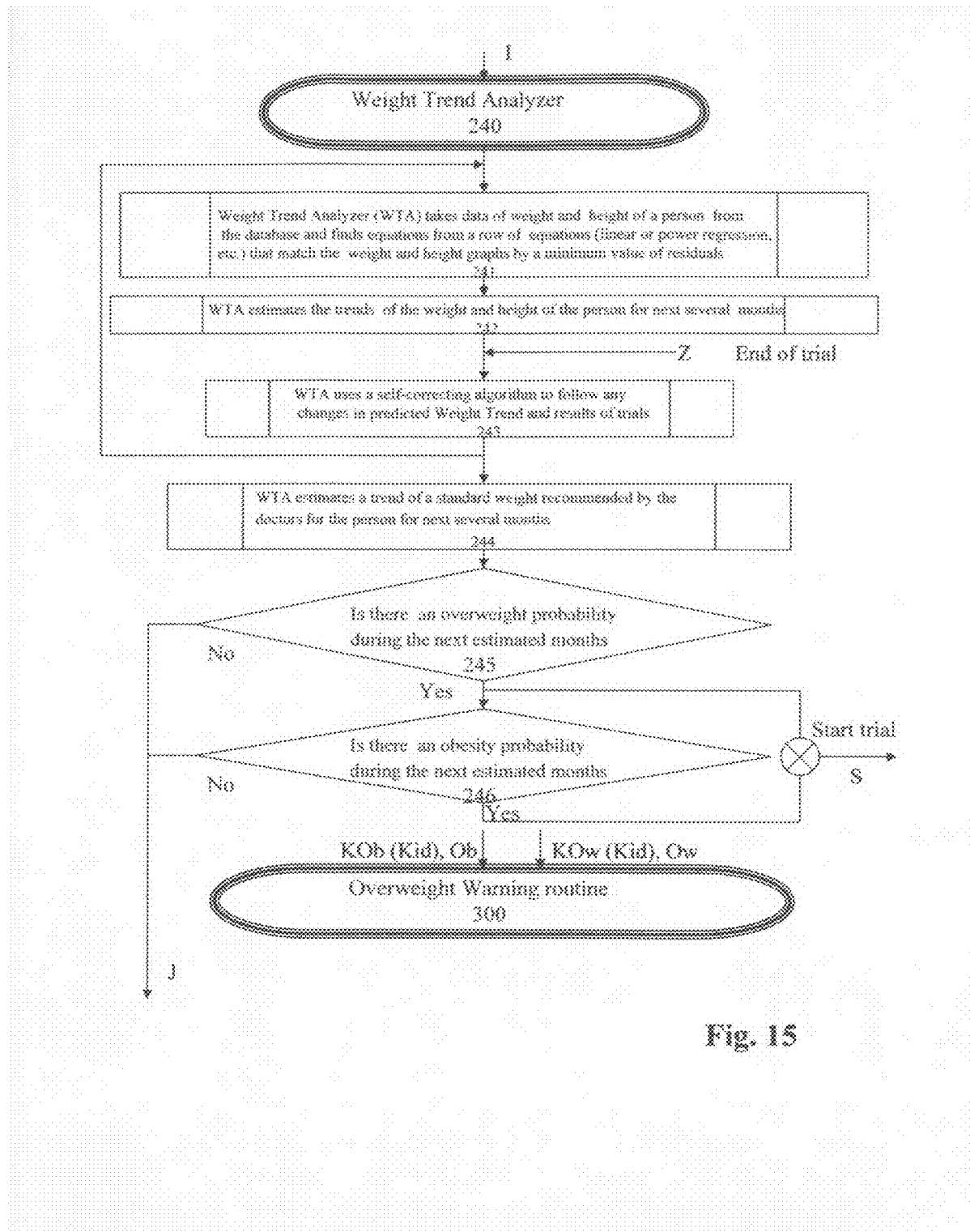
FIG. 15 is a flowchart for the Weight Trend Analyzer routine.
Figure 16:
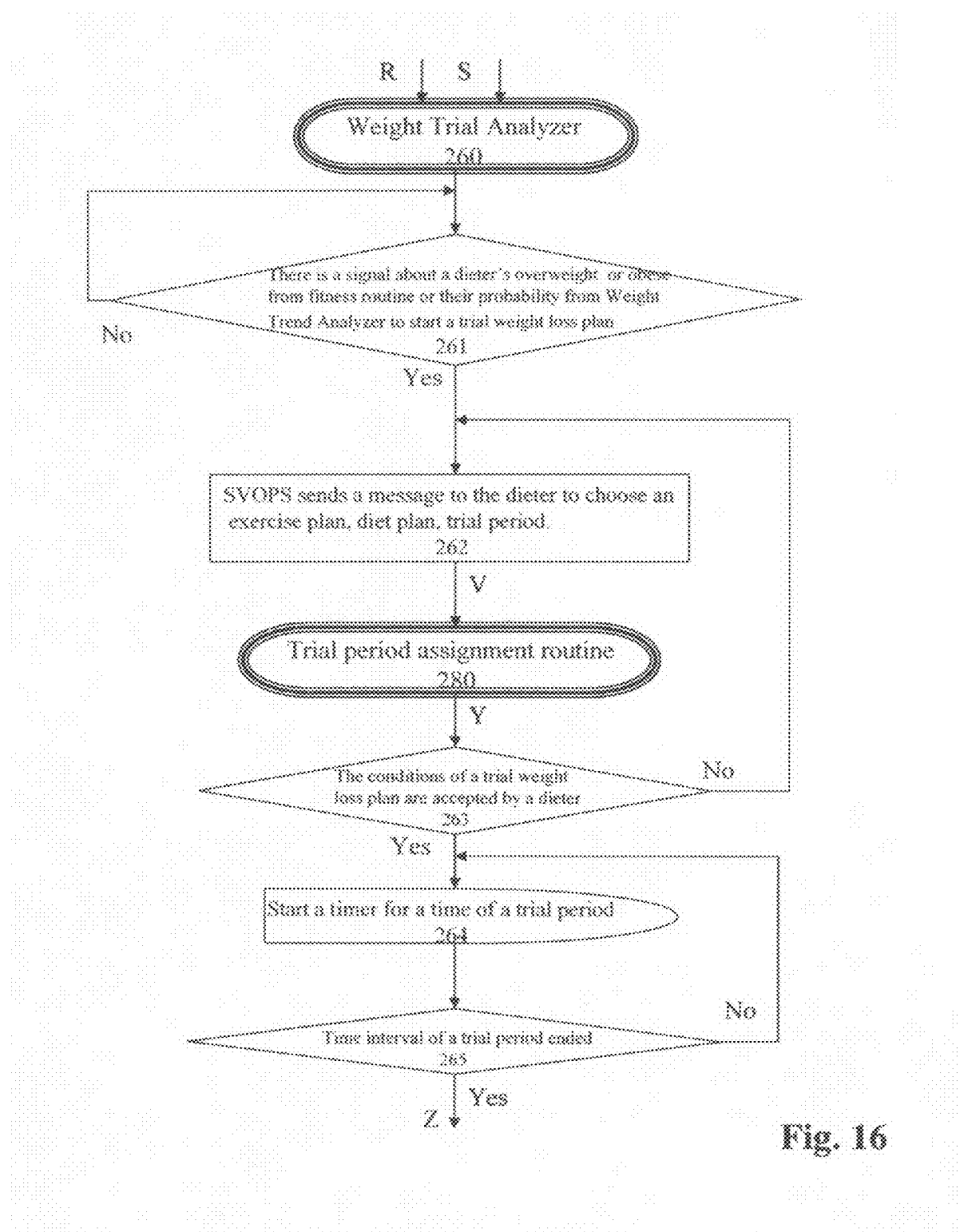
FIG. 16 is a flowchart for the Weight Trial Analyzer routine.

FIG. 15 shows Weight Trend Analyzer routine 240. When SVOPS collects enough weight measurements of a person that it may calculate a future trend of weight progress of a person, Weight Trend Analyzer routine 240 is used. If Weight Trend Analyzer defines that there is an overweight or obesity probability of a person in a certain period of time in the future, SVOPS does not send any warnings to a person or to a person's primary doctor immediately. In contrast, SVOPS starts Weight Trial Analyzer 260 (FIG. 16). This analyzer asks a person to choose an exercise plan, diet plan, to accept a suggested trial period, and to start a weight loss trial plan.

Figure 17:
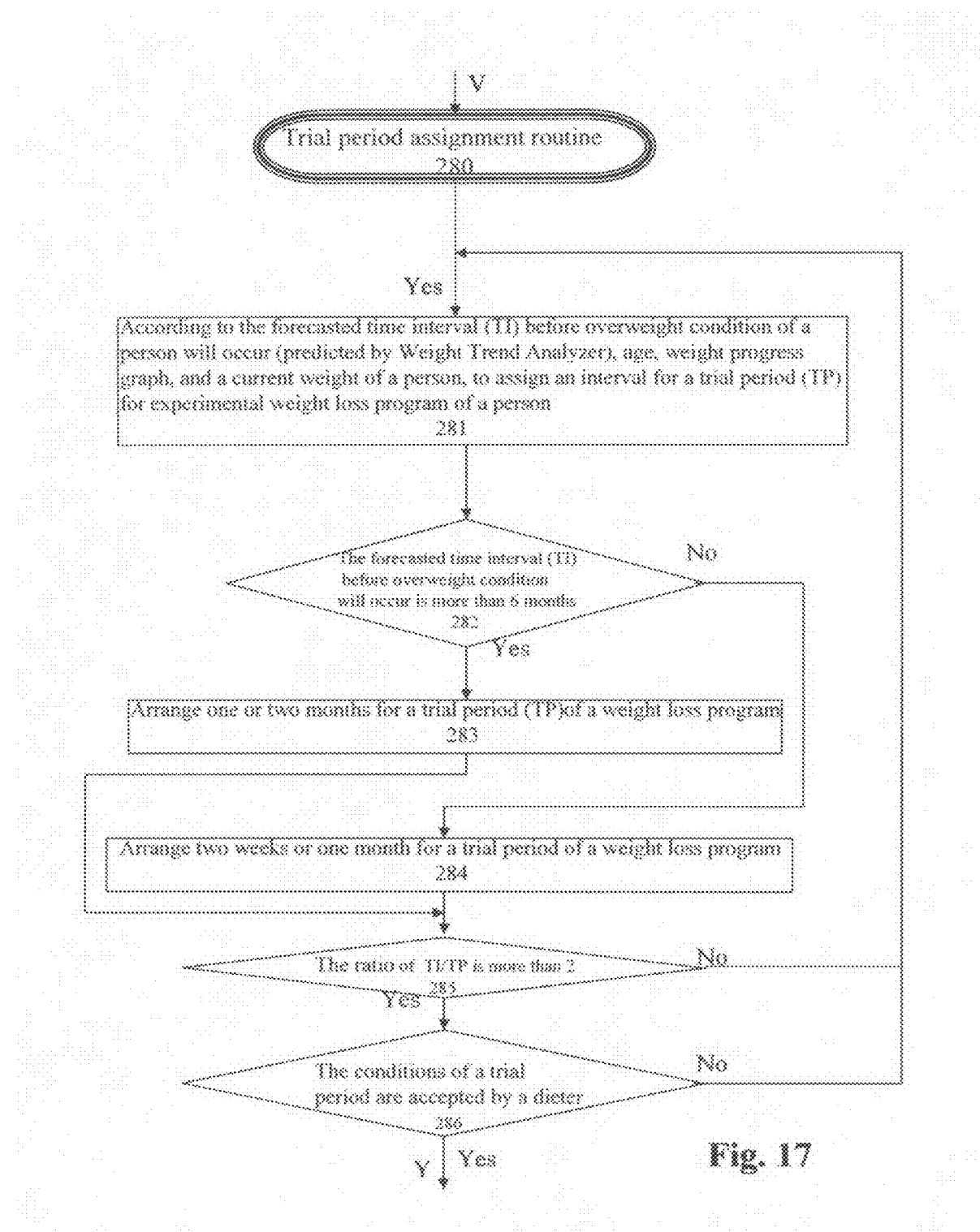
FIG. 17 is a flowchart for the Trial Period Assignment routine.

FIG. 17 shows Trial Period Assignment routine 280. This routine calculates a period of time for weight loss trial plan and suggests to a person to accept a trial period.

If a result of a weight loss trial period is negative, SVOPS may send a warning at the person's discretion to the person or/and to a person's primary doctor by use of the Overweight Warning routine 300 (see FIG. 18) and a communication device 18. The Decision routine 320 (FIG. 19) shows the activities of the person to be assured that his/her progress with the chosen diet and exercises plans is good.

Figure 20:
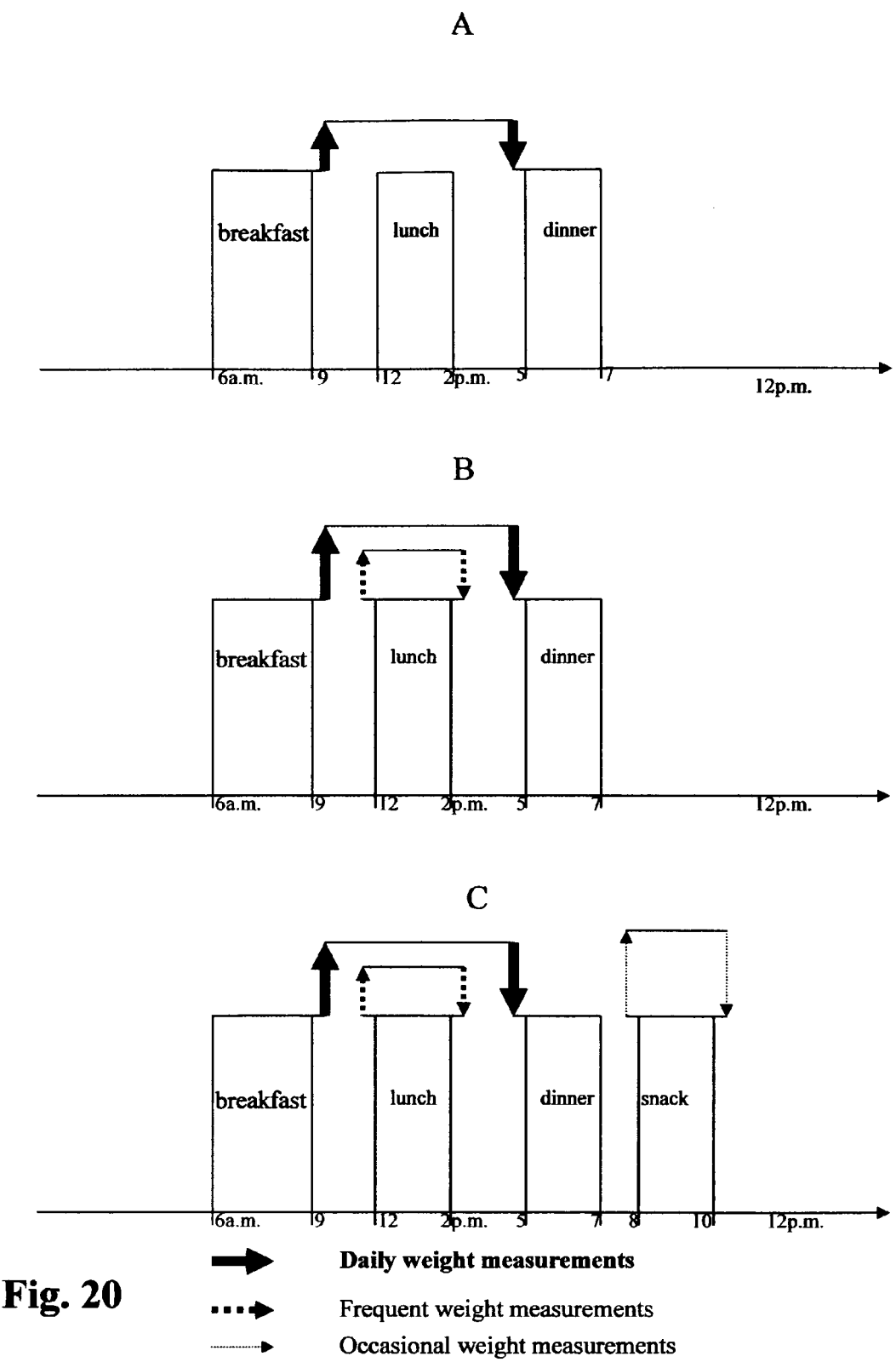
FIG. 20 is a Weight Acquiring graph.

FIG. 20 shows an approximate diagram of everyday occupant's 2, 4, and 6 times per day weight measurements in a vehicle by SVOPS. There may be other variants of occupant weight measurements in a vehicle.

FIGS. 21, 22, 23, 24, and 25 show materials related to a problem of weighing a driver and a passenger in a vehicle: methods of the driver and passenger weighing in a vehicle are used, structures of the driver and passenger weighing apparatus (WAPP), location of weighing devices in a vehicle, etc. The descriptions of FIGS. 21 to 25 are given for a basic structure of WAPP that uses two weighing devices for weighing an individual in a vehicle. In this structure of WAPP, a weighing platform of the first weighing device is located in an individual's car seat and measures the weight of a portion of the individual's body located in the car seat. The weighing platform of the additional weighing device of WAPP is located under individual's feet and fixed or retractable from a suitable part of the vehicle or located in a floor mat and measures the weight of the rest of the individual's body. If in the following descriptions there is no mention of a weighing apparatus which is dedicated just for a driver or a passenger, it means the structure of the apparatus is the same for weighing both a driver or a passenger. Otherwise it will be designated for whom the weighing apparatus will weigh: a driver or a passenger.

Figure 21:
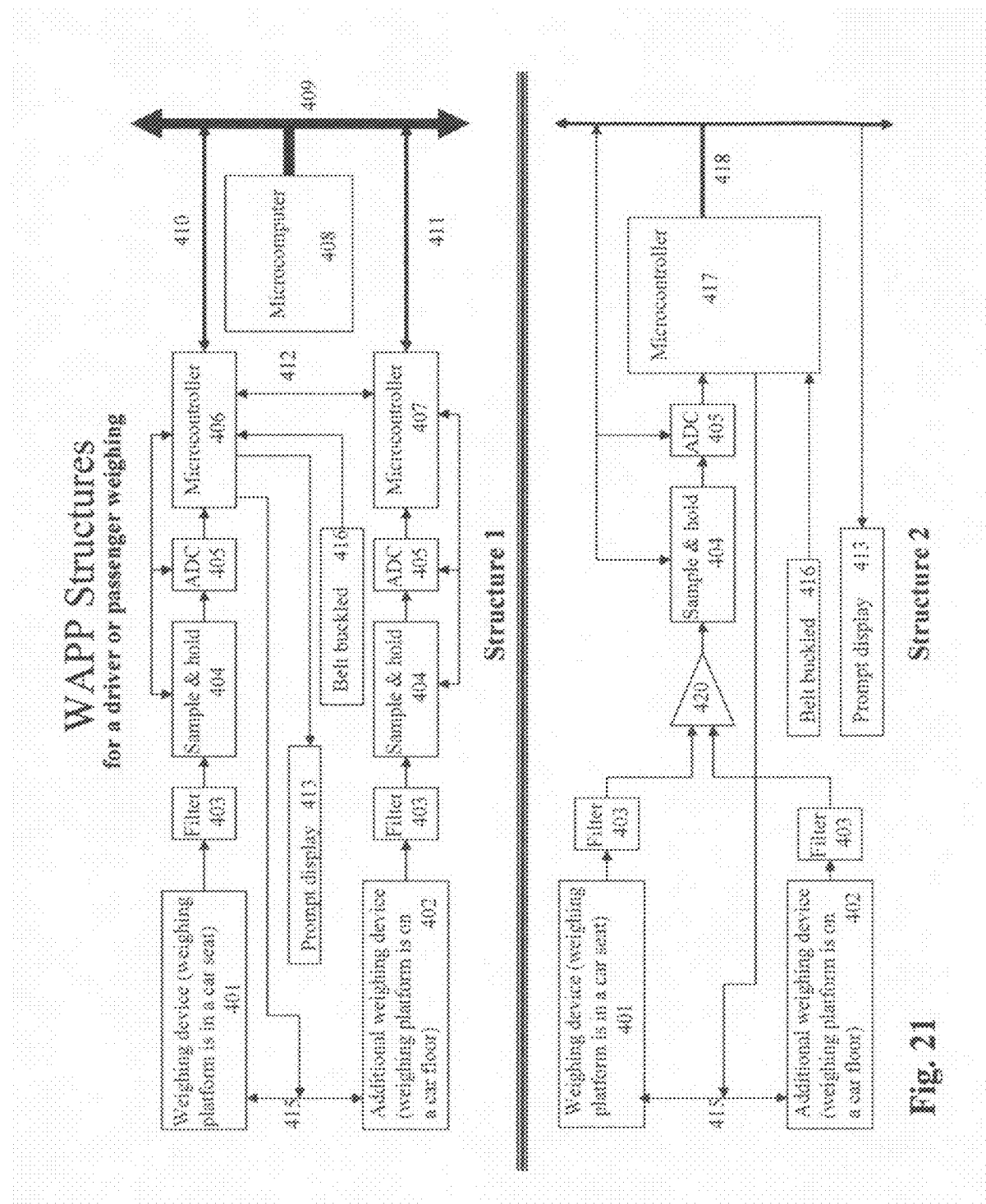
FIG. 21 is a block diagram of a weighing apparatus structures.
Figure 22:
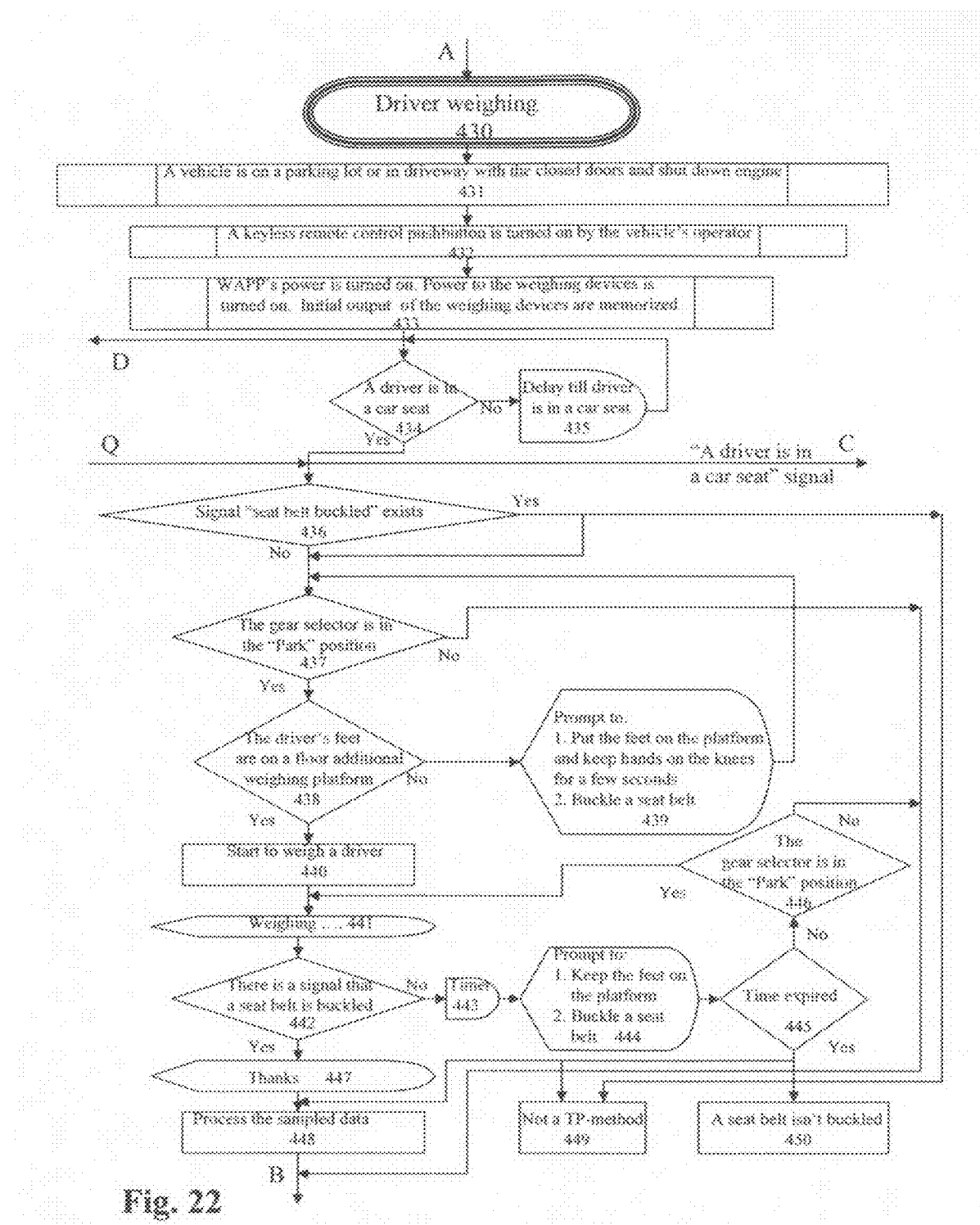
FIG. 22 is a flowchart for the Driver Weighing routine.

FIG. 21 shows the two possible structures of a driver or passenger weighing apparatus that may be used in SVOPS. Both structures receive the same signals from weighing devices of a weighing apparatus. One weighing device 401 is located in a driver or passenger car seat. Another weighing device 402 of a driver or passenger weighing apparatus fixed or retractable from a suitable part of the vehicle or located in a floor mat under the driver's or passenger's feet.

SVOPS is initialized according System Initialization routine 120 (see FIG. 3). When a keyless remote control pushbutton of a parked car 121 is turned on 122 by the vehicle operator, the doors of the vehicle become unlocked 123, and power to SVOPS and a driver weighing apparatus and a passenger weighing apparatus is turned on. When a driver sits down on a driver car seat, driver weighing apparatus (WAPP) weighs 124 a driver by use of Driver Weighing routine 430. System 125 stores the driver's and passenger's weights.

While the preferred weighing apparatus and the methods employed in it for a driver or passenger weighing may be used in any on-board vehicle overweight and obesity preventive system, it may be also employed to control operation of weighing a driver or a passenger in a car safety system or in any other on-board vehicle systems where accurate and convenient weighing of a driver or passenger is required. Because the weighing apparatus may work in a vehicle under control of a certain system, for example, an onboard vehicle overweight preventive system (SVOPS), or under control of a car safety system, this system has to react to a keyless door control system. When the vehicle's operator turns on 432 a pushbutton of a keyless remote control outside of the vehicle in Driver weighing routine 430 (FIG. 22), the power of the weighing apparatus is turned on 433. Signal D activates Passenger Weighing routine 460. Depending on the status of WAPP's work (a separate work or work in the different kinds of systems), control of the WAPP power line circuit may be different. Microcontroller 406 or microcontroller 417 (see WAPP's structure in FIG. 21) receives a signal from the mentioned system that the car doors are unlocked and a driver is coming. Microcontroller 406 or 417 turns on the power line 415 of the weighing platforms and memorizes the output of the weighing device in a driver's car seat and of an additional weighing device that is fixed or retractable from a suitable part of the vehicle or locate in a floor mat under a driver's feet. This data will be used in further processing. WAPP checks 434 if a driver is in the car seat by processing any changes in the data received from the weighing devices and continue 435 to monitor weight of a driver until driver sits down in the car seat.

If WAPP is used in a system that requires information about a position status of a driver, a signal C "A driver is in a car seat" may be used. After that WAPP checks 436 an existence of a "seat belt is buckled" signal 416. If this signal doesn't exist, a measurement of the driver's weight in a parked car will follow by checking 437. If this signal exists, a measurement of a driver's weight according to a previously described TP-method may be not correct, and WAPP sends signal "Not TP-method" in 449. It means that WAPP will use a method of two weighing devices. After step 436 WAPP checks 437 if a gear selector is in the Park position. If a gear selector is not in a Park position, it means that the car is running. In almost all car systems, it is not necessary to get the precise weight of a driver in a running car because there are not any changes in the weight of an individual between a parked or running car. So, it is safer to weigh a driver when the car is in a parked position.

This is a reason for Driver Weighing routine 430 not to weigh a driver in a running car after step 437, and flowchart leaves Driver Weighing routine 430. It will be shown further how to weigh a driver precisely in a running car if it is necessary to do so. If the gear selector is in a Park position in 437, WAPP checks in 438 the existence of the driver's feet on an additional weighing platform, and a driver weighing procedure 440 starts. If the feet are not on an additional weighing platform, WAPP activates in 439 transparent 413 for a driver:

"1. Put the feet on the weighing platform and keep hands on the knees for a few seconds, 2. Buckle the seat belt"

and returns to 437. If the driver's feet on a platform of an additional weighing device, WAPP starts 440 to monitor and memorize driver's weight.

The method described in this invention may use more than one additional weighing device and has several variations, such as, for a driver and a passenger weighing, for weighing in a parked and in a running car, for weighing children and old heavy weak passengers who are unable to buckle a seat belt by themselves.

All these variations of a suggested weighing method are described further.

We now continue to describe the driver weighing routine 430 in a parked car by use of a weighing device in a driver car seat and an additional weighing device that is fixed or retractable from a suitable part of the vehicle or located in a floor mat under the driver's feet. As was mentioned previously, WAPP starts to weigh a driver in 440. Microprocessor(s) collect and process data from a driver car seat weighing device and from an additional weighing device under the driver's feet. The result of weighing will be equal to a sum of a portion of weight of a driver applied to the driver car seat and a portion of weight of a driver applied to the weighing platform of an additional weighing device under the driver's feet.

To eliminate an error of a driver weighing that may appear as a result of touching anything in a car by the driver's hands driver's tah-error), WAPP will continue to weigh 442 a driver according the TP-method until signal 416 that driver's seat belt is buckled appears. This maneuver gives an opportunity to eliminate driver's tah-error because a certain period of time elapses before a driver will buckle the belt, and his/her hands will be in the air and will not touch anything. WAPP will analyze the processed samples of a driver's weight acquired in 440, 441, 442 and get a correct weight 448 of a driver. If signal 416 does not appear in 442, timer 443 will be started, and a prompt to a driver to keep the feet on the additional weighing platform and to buckle a seat belt will be repeated in 444. After that WAPP checks 445 the output of timer 443. If time limited by timer 443 to wait the signal that the driver's seat belt buckled didn't expire, a position of a gear selector will be checked 446. If a gear selector is still in a Park position, WAPP will continue a weighing procedure 441, 442, 443, 444, 445. If a gear selector is not in a Park position, it means that the car is running. WAPP stops weighing a driver and leaves a Driver Weighing routine 430 without any new data in a user weighing database. If it is necessary for any reason to weigh a driver during the trip again, WAPP may do it by signal Q starting from step 436. If signal 416 appears before that time limited by timer 443 expire in 445, WAPP start to process 448 samples of a driver's weight acquired in 440 and 441. Because lack of the signal 416 doesn't allow using TP-method, WAPP will send 449 signal "Not TP-method" and send 450 signal "The seat belt is not buckled".

Figure 23:
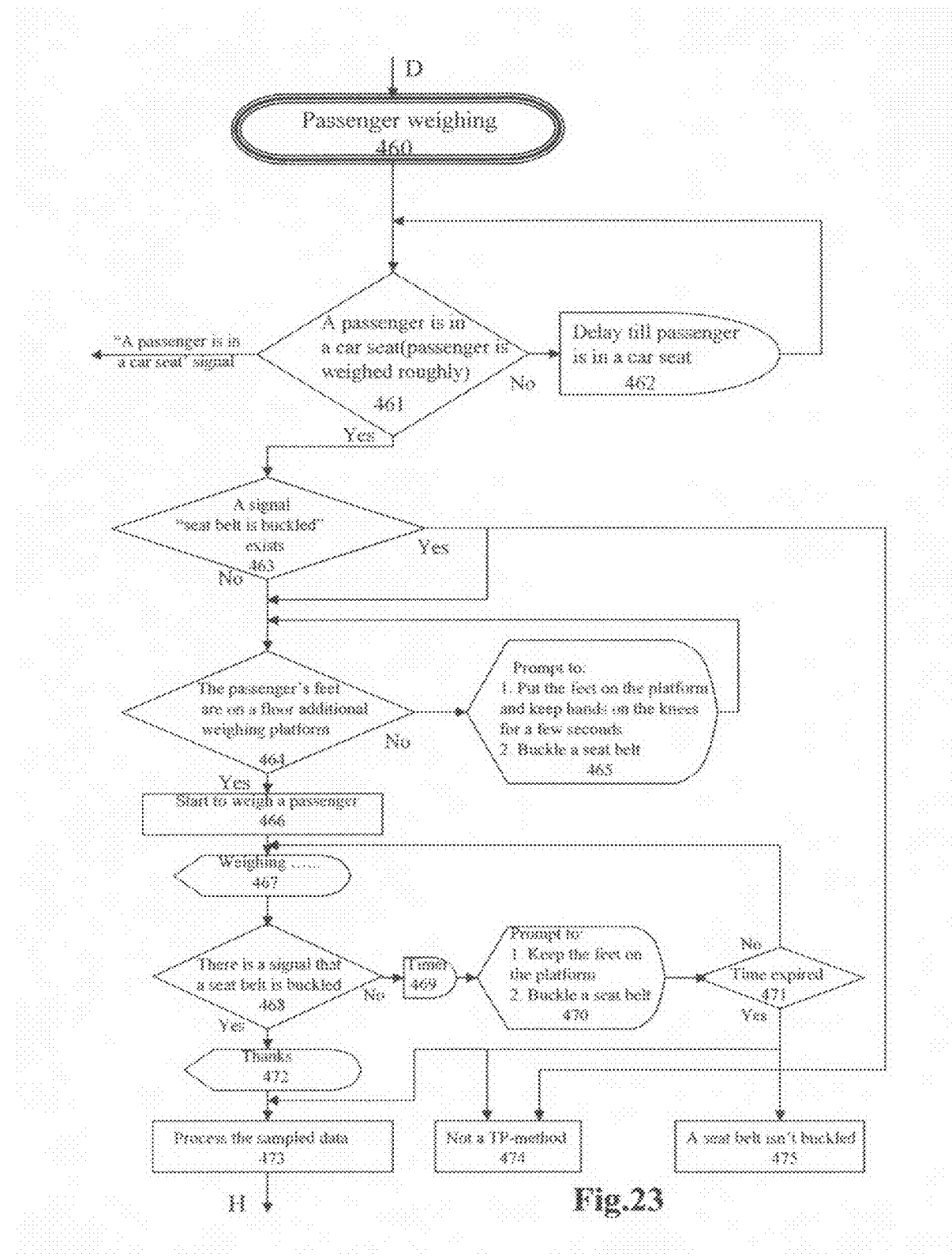
FIG. 23 is a flowchart for the Passenger Weighing routine.

When a passenger is sitting down on a passenger car seat, a passenger weighing apparatus (WAPP) weighs a passenger by use of Passenger Weighing routine 460 (FIG. 23). Let us assume that initially a vehicle is parked, the doors are locked, and nobody is in the car. Because a weighing apparatus may work in a vehicle under control of a certain system, for example, in an on board vehicle overweight preventive system or under control of a car safety system, that system has to react keyless door control system and SVOPS repeats steps 431, 432, 433 of Driver Weighing routine 430, and a power of a weighing apparatus is turned on. After that microcontroller 406 or 417 turns on a power of the weighing platforms as in 433, microcontrollers 406 and 407 or 417 start to provide the Driver Weighing routine 430 and Passenger Weighing routine 460 by collecting the output data of the weighing devices in a driver's and in a passenger's car seats and output data of the additional weighing devices that are fixed or retractable from a suitable part of the vehicle or located in a floor mat under the driver's and passenger's feet. In 461 of Passenger Weighing routine 460, WAPP checks if a passenger is in a car seat by processing any changes in data received from the weighing devices and continues 462 to monitor the weight of a passenger until passenger sits down in a car seat. If WAPP is used in any car system that monitors an existence of a passenger in a car seat during a trip, a signal "A passenger is in a car seat" may be sent by Passenger Weighing routine 460 when a passenger exists in a car seat. The structure of the WAPP for weighing a passenger is the same as for weighing a driver (see FIG. 21). WAPP checks 463 an existence of a passenger "seat belt is buckled" signal 416. If this signal doesn't exist, a measurement of the passenger's weight in a car will follow by checking 464. If this signal exists, a measurement of a passenger's weight according to a described previously TP-method may be not correct, and WAPP sends 474 signal "Not TP-method". It means that WAPP will use a method of two weighing devices and goes back to 464. WAPP checks 464 to see that the passenger's feet are on an additional weighing platform, and a passenger weighing procedure 466 starts if they are. If the feet of a passenger are not on an additional weighing platform, WAPP activates 465 a transparent 413 for a passenger:

1. Put the feet on the weighing platform and keep hands on the knees for a few seconds, 2. Buckle the seat belt", and returns to 464.

If the passenger's feet are on a platform of an additional weighing device, WAPP starts 466 to monitor 467 and memorizes the passenger's weight. Microprocessors 406, 407, or 417 collect data from a passenger car seat weighing device and from an additional weighing device under the passenger's feet. The result of weighing will be equal to a sum of a portion of the weight of a passenger applied to the passenger car seat and a portion. of the weight of a passenger applied to the weighing platform of an additional weighing device under the passenger's feet. To eliminate an error in a passenger's weight that may appear as a result of touching anything in a car by the passenger's hands (passenger's tah-error) during a weighing, WAPP will continue 467, 468 to weigh a passenger according a TP-method until 468 a signal 416 that passenger's "seat belt is buckled" appears. This maneuver gives an opportunity to eliminate passenger's tah-error because a certain period of time elapses before a passenger will buckle the seat belt, and his/her hands will be in the air and will not touch anything. WAPP will analyze the processed 473 samples of a passenger's weight acquired in 466, 467, 468 and get a correct additional weighing platform, WAPP activates 465 a transparent 413 for a passenger:

1. Put the feet on the weighing platform and keep hands on the knees for a few seconds,
2. Buckle the seat belt", and returns to 464.

If the passenger's feet are on a platform of an additional weighing device, WAPP starts 466 to monitor 467 and memorizes the passenger's weight. Microprocessors 406, 407, or 417 collect data from a passenger car seat weighing device and from an additional weighing device under the passenger's feet. The result of weighing will be equal to a sum of a portion of the weight of a passenger applied to the passenger car seat and a portion. of the weight of a passenger applied to the weighing platform of an additional weighing device under the passenger's feet. To eliminate an error in a passenger's weight that may appear as a result of touching anything in a car by the passenger's hands (passenger's tah-error) during a weighing, WAPP will continue 467, 468 to weigh a passenger according a TP-method until 468 a signal 416 that passenger's "seat belt is buckled" appears. This maneuver gives an opportunity to eliminate passenger's tah-error because a certain period of time elapses before a passenger will buckle the seat belt, and his/her hands will be in the air and will not touch anything. WAPP will analyze the processed 473 samples of a passenger's weight acquired in 466, 467, 468 and get a correct driver's touch screen, and a driver may have a dialogue with the system. If there is neither of these two states, a system remains passive (touch screen is dark), creates delay 134 until the parking or heavy traffic situation occurs.

Figure 5:
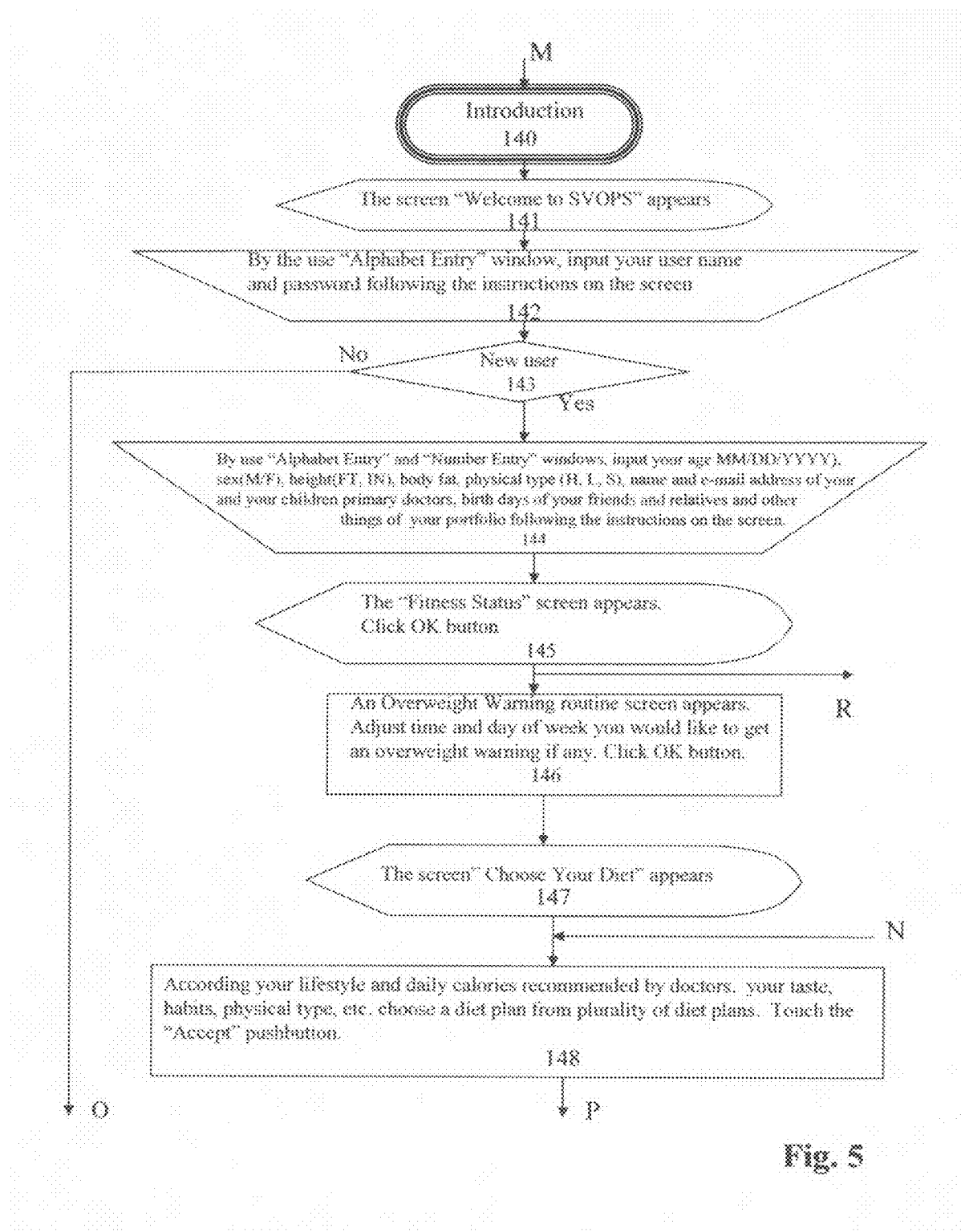
FIG. 5 is a flowchart for the Introduction routine.

When the system is activated, the screen "Welcome to SVOPS" appears 141 through the Introduction routine 140 (FIG. 5). The user is invited to input his/her name and password 142 by use of the "Alphabet Entry" pop-up window (FIG. 13). The system checks the name and password and recognizes if the user is a new user 143. If the user is a new user, the system asks him or her to input 144 his or her age, sex, height, body fat, physical type (H—a highly active individual, L—a limitedly active individual, S—a sedentary individual), name and e-mail address of his/her and his/her children primary doctors, birthdays of relatives and friends and other things of his/her portfolio following the instructions on the screen by use of the "Alphabet Entry" window and "Number Entry" (FIG. 14) window. After the user has entered the above data, the "Fitness Status" screen appears 145. It shows the weight for the user recommended by the doctors and calories to be consumed per day. The user can use the "Fitness Status" screen to choose the number of pounds to lose daily, and the user will find the number of the calculated days needed to lose extra pounds in the "day" box. or the user can choose the number of days he/she wants to lose the extra pounds. In this case, the Fitness Status" screen will show the calculated pounds to lose daily. An Overweight Warning routine screen appears 146. A user is invited to enter time and day of week that the user would like to receive an overweight warning, if any. It means that any overweight warning (to the user, to his/her primary doctor, to his/her children primary doctor, etc.) may be sent only at user's discretion. The screen "Choose Your Diet" 147 appears. The system suggests 148 to the user to choose a diet plan from a plurality of diets in the Diets Database according his or her weight, and daily calories, recommended by doctors or based upon user's taste, habits, physical type, etc.

Figure 25:
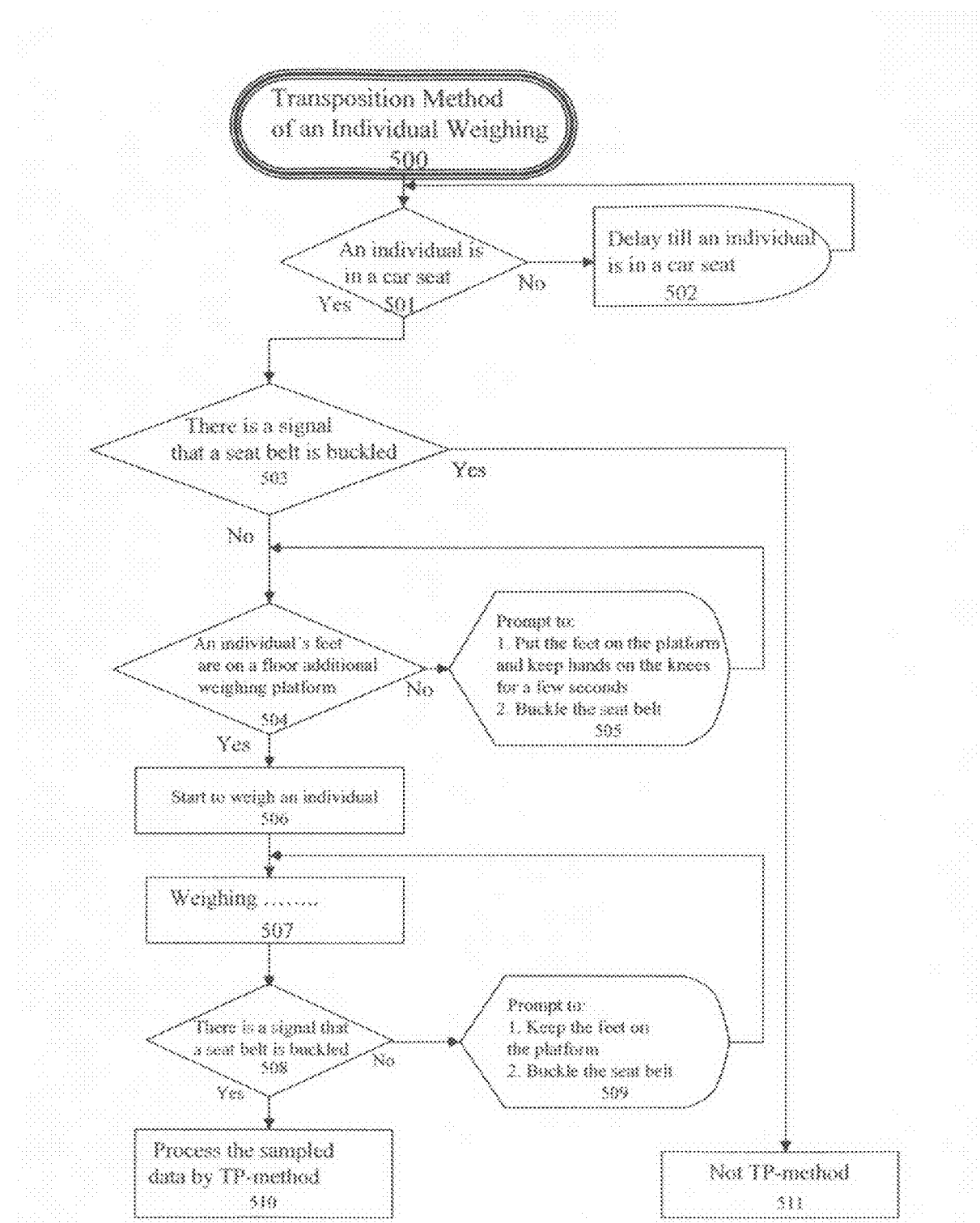
FIG. 25 is a flowchart for the Transposition Method of an individual in a vehicle weighing routine.
Figure 26:
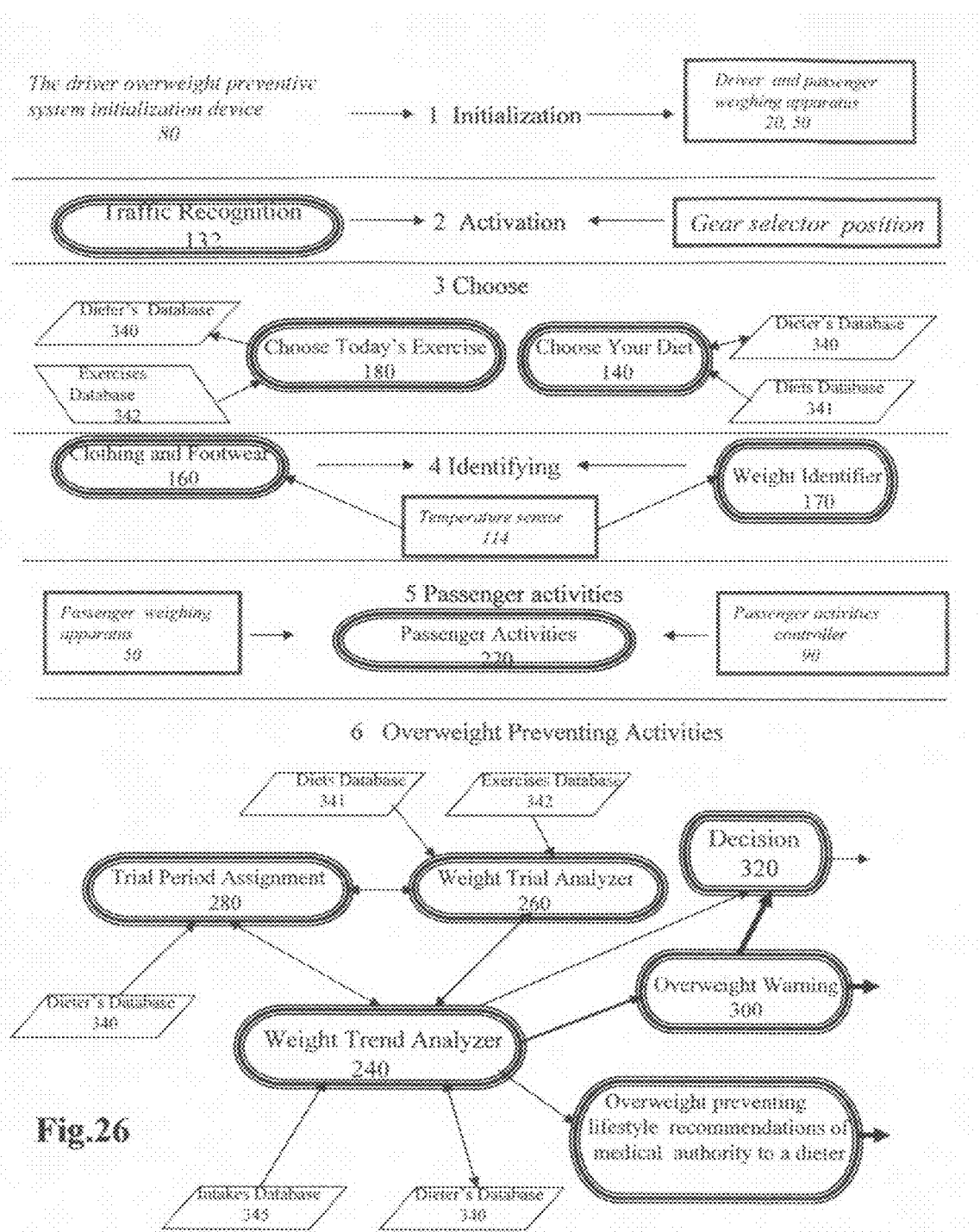
FIG. 26 is a block diagram of the interconnection of the software routines during the dieter's activities in a vehicle.

FIG. 25 is a flowchart for a Transposition Method (TP-method) of Weighing an individual in a vehicle routine 500. This method is the same for both the driver and passenger in a vehicle. Assume that initially a vehicle is parked, the doors are locked, and nobody is in a car. WAPP or system in which it is used reacts to a keyless door control system, and power of WAPP and it's weighing devices is turned on after an operator of a car pushes a button of a car keyless door control system to open the doors. Microcontrollers 406 and 407 or 417 start to provide the Driver Weighing 430 and Passenger Weighing 460 routines by collecting the output data of the weighing devices in a driver's and in a passenger's car seats and output data of the additional weighing devices that are fixed or retractable from a suitable part of the vehicle or located in a floor mat under the driver's and passenger's feet. Assume there is a signal to weigh an individual in a car, and we will show now how the Transposition Method of an Individual Weighing routine 500 (FIG. 25) works. In 501 WAPP checks if an individual is in a car seat by processing any changes in a data received from the weighing devices and continues 502 to monitor weight of an individual until an individual sits down in a car seat. WAPP checks in 503 an existence of an individual "Seat belt is buckled" signal 416. If this signal doesn't exist, a measurement of an individual's weight in a car will follow. If this signal exists, a measurement of an individual's weight can not use TP-method. WAPP sends 511 a signal "Not TP-method" and leaves Transposition Method of an individual Weighing routine 500. If a signal "seat belt is buckled" doesn't exist, WAPP checks 504 an existence an individual's feet on an additional weighing device, and weighing of an individual 506 starts if any. If the feet of an individual are not on an additional weighing device, WAPP activates a transparent 413 for an individual:

"1. Put the feet on the weighing device and keep hands on the knees for a few seconds,
2. Buckle the seat belt", and returns to 504.

If the individual's feet are on a platform of an additional weighing device, WAPP starts 506 to monitor 507 and memorize an individual's weight. Microprocessors 406 and 407, or 417 collect data from an individual car seat weighing device and from an additional weighing device that is fixed or retractable from a suitable part of the vehicle or located in a floor mat under the individual's feet. The result of weighing will be equal to a sum of a portion of weight of an individual applied to an individual's car seat and a portion of weight of an individual applied to the weighing platform of an additional weighing device under the individual's feet. WAPP checks a signal "Seat belt is buckled" in 508. If the signal doesn't exist, WAPP activate 509 transparent 413 for an individual:

1. Keep the feet on the weighing platform,
2. Buckle the seat belt", and returns to 507.

To eliminate an error in an individual's weight that may appear as a result of touching anything in a car by an individual's hands (individual's tah-error) during a weighing, WAPP will continue 507, 508 to weigh an individual until 508 a signal 416 that individual's "seat belt is buckled" appears. This maneuver gives an opportunity to eliminate individual's tah-error because a certain period of time elapses before an individual buckles the belt, his/her hands will be in an air and will not touch anything. WAPP will analyze the processed 510 samples of an individual's weight acquired in 506, 507, and get a correct weight of an individual. The described transposition method of weighing an individual in a car is simple but requires a certain sequence of steps during weighing.

The following is a weighing procedure to teach a driver or a passenger how to weigh one's self in a car:

1. When you sit down in the car seat, put your feet on a weighing platform under your feet, 2. Keep your hands on your knees (don't touch anything in the car by hand) and don't push your back against the back of the car seat for a few seconds, 3. Buckle the seat belt.

This sequence of steps is natural for an individual in a vehicle, but before beginning and during the procedure an activated transparent or voiced announcement about this procedure may be used just in case.

It is necessary to highlight that even if an individual does not keep his/her hands from anything in the car according step 2 of the procedure, WAPP will get a weight close enough to the weight of an individual because of the use of two weighing devices.

FIG. 21 is a block diagram of an on-board vehicle weighing apparatus. In the first embodiment (structure 1), that employs separate microcontrollers for a weighing device and an additional weighing device, one part (a car seat channel) of the weighing apparatus consists of weighing device 401, filter 403, sample and hold device 404, analog-to-digital converter 405, and microcontroller 406. Filter 403 includes a conditional circuit.

The second part (feet channel) of the weighing apparatus, that serves for an additional weighing device, consists of an additional weighing device 402, filter 403, sample and hold device 404, analog-to-digital converter 405, and microcontroller 407.

There are interfaces 410 and 411 between microcontrollers 406 and 407 and microcomputer 408 and it's bus 409 for a data and control signals exchange between the two microcontrollers and microcomputer. Line 412 is used for purposes of synchronization of the two microcontrollers. Prompt display 413 is used to show directives to an individual during a weighing procedure. Microcontroller 406 of a car seat channel uses a line 415 to initialize both a weighing device 401 of a car seat channel and an additional weighing device 402 of a feet channel by turning on their power supply line. A switch 416 sends a signal to a microcontroller 406 when a car seat belt is buckled by an individual.

In this embodiment (structure 1), a microcontroller 406 or microcomputer 408 receives through a bus 409 a signal to initialize the weighing devices. Microcontroller 406 of a car seat channel turns on power supply lines of both a weighing device 401 whose weighing platform is in a car seat and an additional weighing device 402 that is fixed or retractable from a suitable part of the vehicle or located in a floor mat. After that two analog signals appear. The first signal appears as an output of weighing device 401, and this signal is directly proportional to the portion of weight of an individual applied to the car seat. The second signal appears as an output of an additional weighing device 402, and this signal is directly proportional to the portion of weight of an individual applied to the weighing platform through the individual's feet. Each of these two signals appears at the output of the corresponding filter 403 after the conditioning and filtering. Microcontrollers 406 and 407 control the sample and hold devices 404 and the analog-to-digital converters 405 to acquire samples of weight and transform them to a digital form to process them. Microcontroller 406 collects data from microcontroller 407 through interfaces 410 and 411 and bus 409 and adds the samples of weight acquired at the same time by both a car seat channel and a car feet channel. The result of processing is directly proportional to the whole weight of an individual in a car seat and who during a weighing procedure keeps his/her feet on a weighing platform of an additional weighing device located under the individual's feet.

A microcomputer 408 may exist in this embodiment depending on the weighing apparatus task.

In the second embodiment (FIG. 21, structure 2), that employs only one microcontroller for a weighing device and an additional weighing device, one part (a car seat channel) of the weighing apparatus consists of the weighing device 401, filter 403, summing circuit 420, sample and hold device 404, analog-to digital converter 405, and microcontroller 417. Filter 403 includes a conditional circuit.

The second part (feet channel) of the weighing apparatus, that serves as an additional weighing device, consists of an additional weighing device 402, filter 403, and (as a car seat channel) uses the same summing circuit 420, a sample and hold device 404, analog-to-digital converter 405, and microcontroller 417. There is a bus 418 of microcontroller 417 for a data and control signals exchange between the microcontroller and microcomputer of a possible system. Prompt display 413 is used to show directives to an individual during a weighing procedure. Microcontroller 417 uses line 415 to initialize both a weighing device 401 of a car seat channel and an additional weighing device of a feet channel by turning on their power supply line. A switch 416 sends a signal to a microcontroller 417 when a car seat belt is buckled by an individual.

In this embodiment (FIG. 21, structure 2) microcontroller 417 receives through a bus 418 a signal to initialize the weighing devices. Microcontroller 417 turns on the power supply lines of both a weighing device 401 which weighing platform is in a car seat and an additional weighing device 402 which weighing platform is fixed or retractable from a suitable part of the vehicle or located in a floor mat. After that two analog signals appear. The first signal appears as an output of weighing device 401, and this signal is directly proportional to the portion of weight of an individual applied to the car seat. The second signal appears as an output of an additional weighing device 402, and this signal is directly proportional to the portion of weight of an individual applied to the weighing platform through the individual's feet. Each of these two signals appears at the output of the corresponding filter 403 after the conditioning and filtering. An analog summing device 420 adds these two signals, and as a result, the input of the sample and hold device 404 is directly proportional to a whole weight of an individual in a car seat who during a weighing procedure keeps his/her feet on the weighing platform of an additional weighing device under an individual's feet. Microcontroller 417 controls the sample and hold device 404 and the analog-to-digital converter 405 to acquire samples of weight and transform them to a digital form and to process them according to a program that is stored in microcontroller 417.

Figure 24:
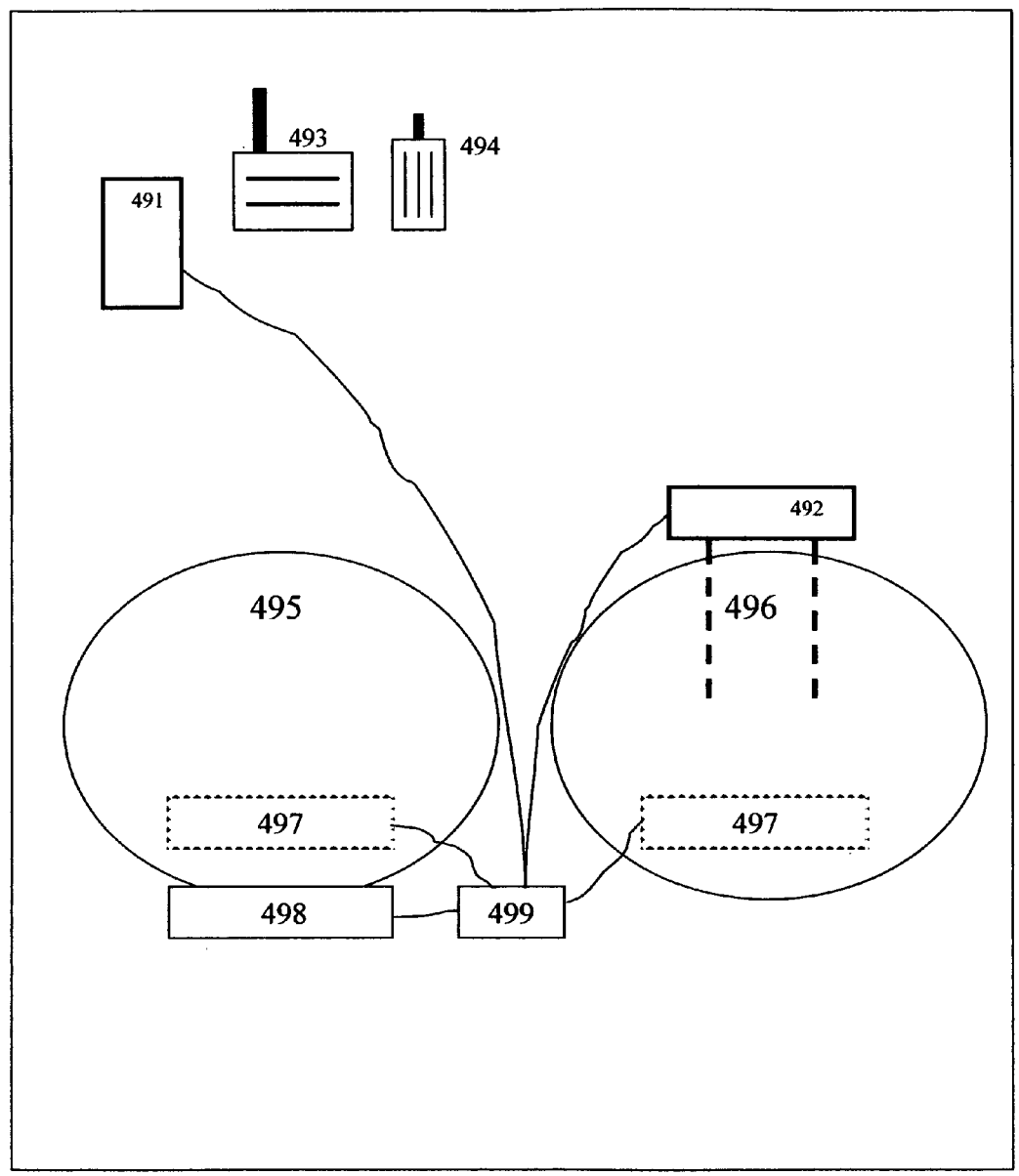
FIG. 24 is a block diagram of a weighing apparatus weighing platform location.

FIG. 24 shows a block diagram of location of weighing platform 497 of a driver weighing device in car seat 495, weighing platform 491 of the driver additional weighing device, weighing platform 492 of passenger additional weighing device, box 499 including conditioning electrical circuit for summing up and processing (filtering, sampling, converting to digital form, and processing by microcontroller) of electrical signals from both driver weighing platform in a car seat and weighing platform of driver additional weighing device on a footrest and a box of a driver car seat back controller 498 inside a car for one of embodiments of SVOPS.

A weighing platform of a driver additional weighing device (DAD) 491 is located on the footrest under the driver's feet close to the brake 493 and gas 494 pedals. A weighing platform of a passenger additional weighing device (PAD) 492 is retractable from the passenger car seat frame and located under the passenger's feet.

The driver car seat 495 (includes a driver weighing platform 497) and a front passenger car seat 496 (includes a passenger weighing platform 497) have to be in a position that is convenient for a driver and a passenger.

The system then goes into the Clothing and Footwear routine 160 (FIG. 6) and asks the new user to give a clue about his or her clothing and footwear 161 by touching in 162 or 163 a corresponding item on the touch-screen. If the user asked in 143 is not a new user, the system goes to the Weight Identifier routine 170 (FIG. 7) and recognizes if the weight of the user has changed 171 by two or more pounds since last weight measurement. Of course, one skilled in the art can determine that other weight ranges can be programmed into the unit. If the weight has not changed by two or more pounds since the last measurement, the program goes directly to Choose Today's Exercise Routine 180. If the weight has changed, the system tries to find the reason for the change. To find out if the weight change is correlated to a weather change, SVOPS checks the outside temperature sensor 172. It also asks 173 the user if he/she has changed clothing and/or are since the last weight measurement. If the answer is "yes", the system asks if the clothing has changed 174 or footwear 175. If clothing or footwear has changed, the program goes back to the Clothing and Footwear routine 160 where the dieter shows on the touch-screen the items of the changed clothing or footwear. If the user answers in the Weight Identifier routine 170 that nothing has changed, the system at a user's discretion gives a warning to the user that he/she has overeaten today and asks him/her to exercise more today 176 and the program goes to the Choose Today's Exercise routine 180 (FIG. 8) and Exercise Database. On the main screen 181 he/she touches the "Choose Today's Exercises pushbutton 182. On the screen "Exercise Selection" that appears 183 the user chooses his/her today's exercises according to his/her taste, habits, physical type 184, 185 and according to his/her weight and daily calories intake, recommended by medical authorities.

Figure 9:
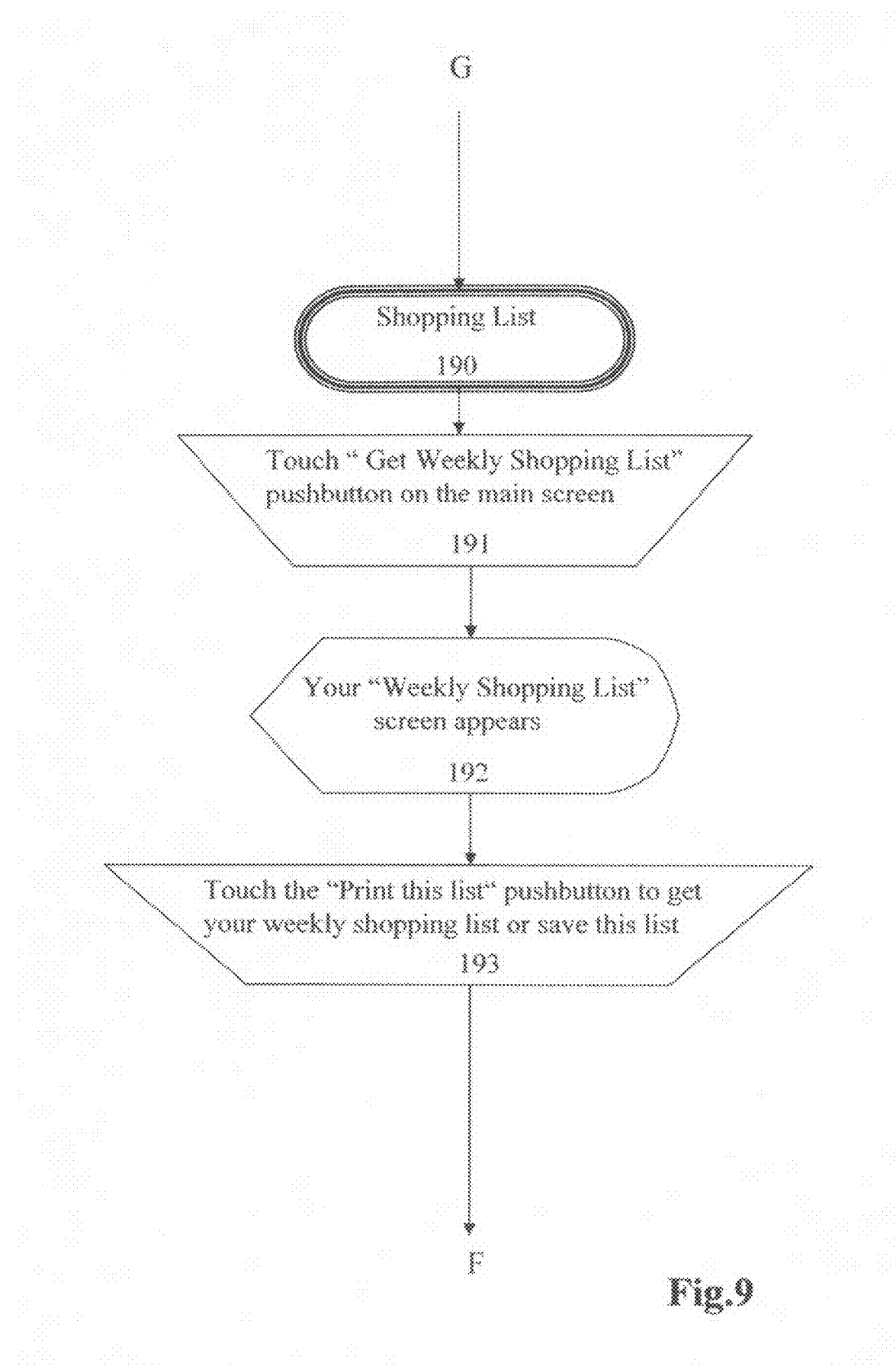
FIG. 9 is a flowchart for the Shopping List routine.

To get a weekly shopping list, the dieter uses the "Shopping List" routine 190 (FIG. 9). By touching the "Get Weekly Shopping List" pushbutton on the main screen 191, the dieter gets 192 the "Weekly Shopping List" screen. The dieter can check the food items and values and saves this list or prints it out 193.

Figure 10:
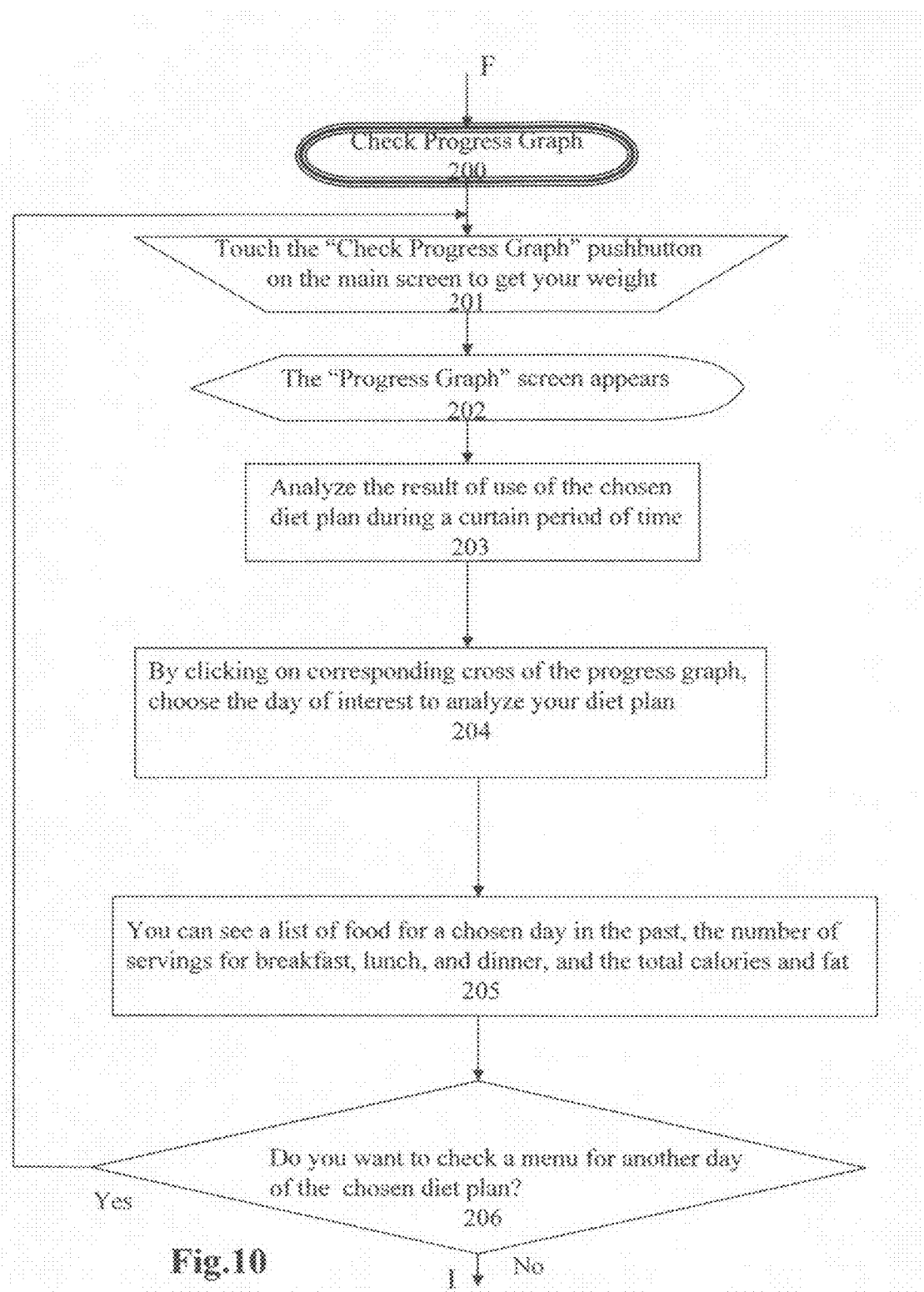
FIG. 10 is a flowchart of the Check Progress Graph routine.

FIG. 10 shows the Check Progress routine 200 by use of which the dieter can review his/her weight progress graph and see his or her menu on a selected day in the past of the chosen diet plan. This is useful for observing the effect of a certain menu on the weight progress graph. By touching 201 the "Check Progress Graph" pushbutton on the main screen the dieter will get 202 the "Progress Graph" screen with the dieter's weight progress graph on it. To observe the effect 203 of a certain menu on the weight progress graph the dieter has to touch 204 the corresponding cross on the progress graph. The dieter can see a list of food items for a chosen day in the past and its effect on a weight progress graph, a number of servings for breakfast, lunch, and dinner, and the total calories and fat 205. The dieter can check a menu for any day of his/her diet plan 206.

When a number of daily weight measurements of a user becomes enough to make a correct forecast for a user overweight probability in the future and give a chance for this individual to prevent overweight in the future, SVOPS executes Weight Trend Analyzer routine 240 (FIG. 15). Weight Trend Analyzer (WTA) collects measurements of weight and height of a person and estimates an overweight or obesity probability of a person during several next months. In 241 WTA by collecting measurements of weight and height of a person finds equations that match the weight and height graphs. After that, WTA estimates 242 the trends of the weight and height of the person. To improve the correctness of the calculated weight trend, WTA employs 243 the results of the previous calculation of a trend. In 244 WTA estimates a trend of weight recommended for a person. WTA estimates probability of a person's overweight (245) or obesity (246) during following several months. If there is an overweight or obese probability during the next several months, WTA doesn't send any warning to a person but sends a signal "Start trial" to Weight Trial Analyzer 260 (FIG. 16) to start a trial weight loss plan.

Figure 18:
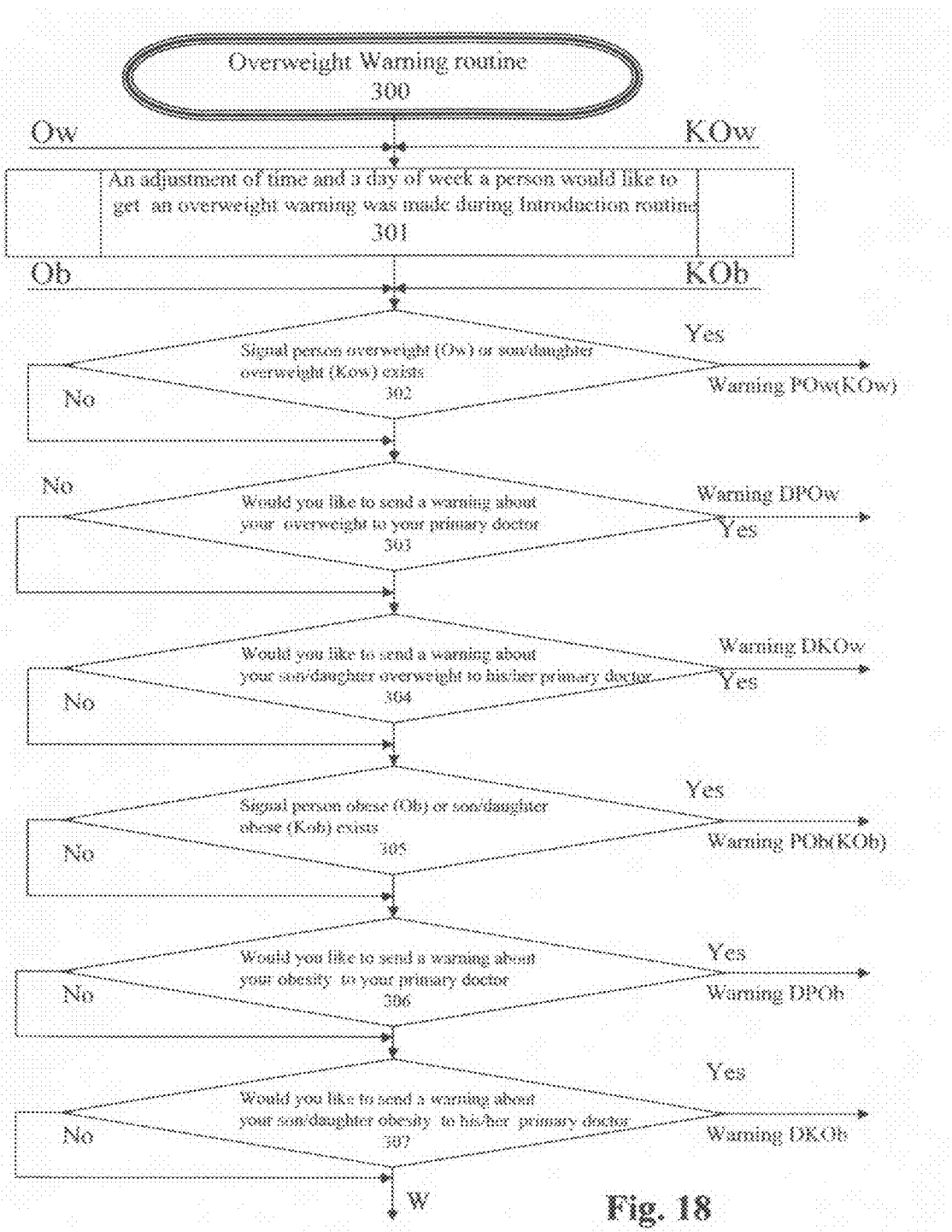
FIG. 18 is a flowchart for the Overweight Warning routine.
Figure 19:
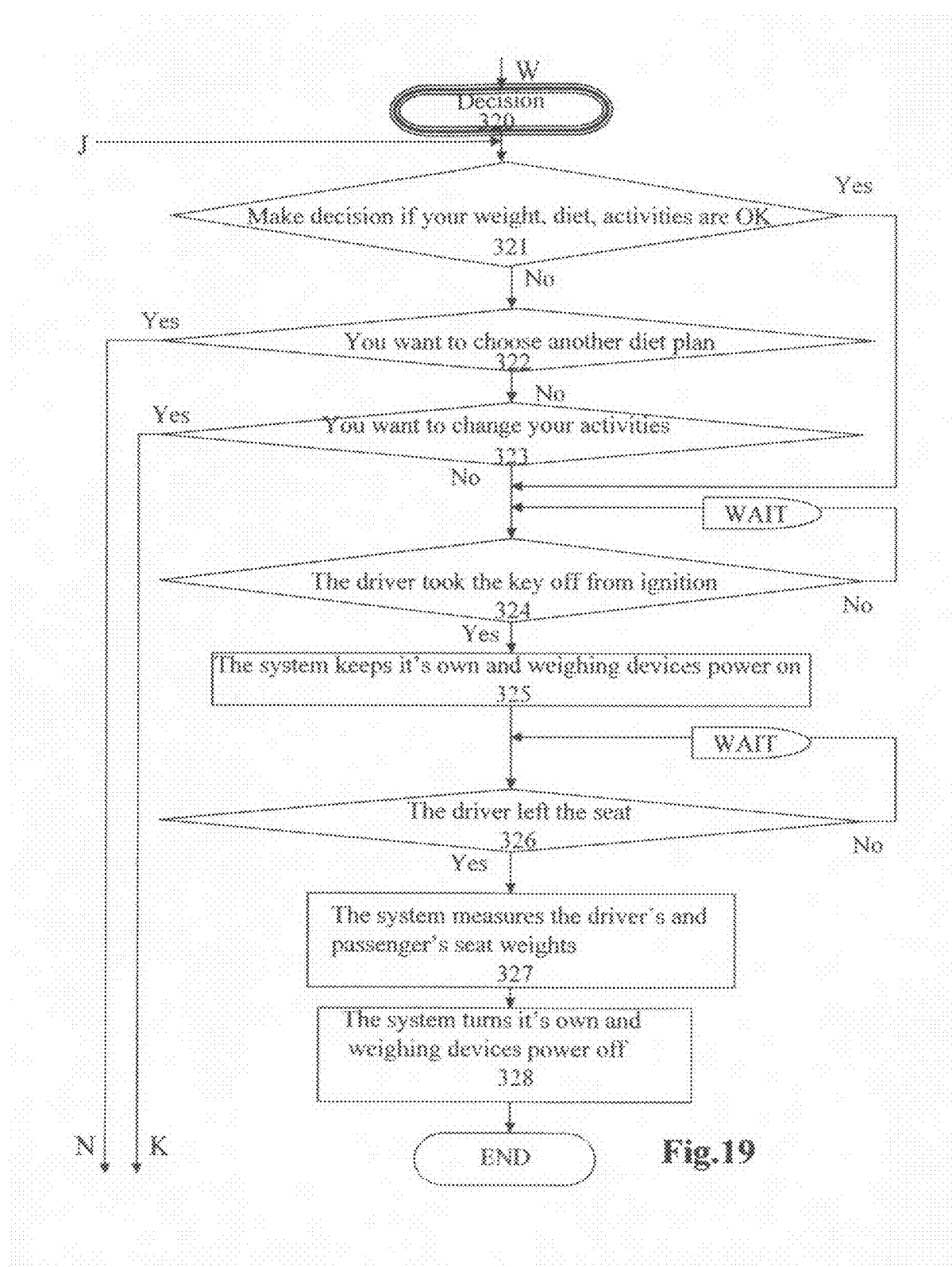
FIG. 19 is a flowchart for the Decision routine.

Weight Trial Analyzer 260 checks 261 to see if there is a signal about a person's overweight or obesity from fitness routine or probability from Weight Trend Analyzer. If any of these signal appears, SVOPS sends 262 a message to a person to choose an exercise plan, diet plan, to agree to a trial period, and runs Trial Period Assignment routine 280 (FIG. 17). This routine assigns 281 an interval for a trial period (TP). Trial Period Assignment routine 280 checks 282 the length of forecasted time interval (TI) before overweight condition will happen and assigns in 283 or 284 a trial period for a weight loss plan. After that routine checks 285 to see if trial weight loss plan is shorter than TI and a TP is accepted by a person 286. After that SVOPS returns to Weight Trial Analyzer routine 260 and checks 263 if all conditions of a trial weight loss plan are accepted by a person and triggers 264 a timer to count time of a trial period. When a time interval of a trial period ends 265, Weight Trial Analyzer 260 sends a signal Z to 243 of Weight Trend Analyzer 240. After that Weight Trend Analyzer checks the results of a trial weight loss program, and if the result of a trial weight loss program is negative, it sends appropriate warning signals (Kob—obesity of a kid, Ob—obesity of a person, KOw overweight of a kid, Ow—overweight of a person) to Overweight Warning routine 300 (FIG. 18). This routine at person's discretion will send overweight or obese warnings 302, 303, 304, 305, 306 and 307 to an overweight or obese person (POw, POb), to a primary doctor of a person (DPOw, DPOb), to owner of a car whose child or teenager is overweight or obese (KOw, KOb), to a primary doctor of a person's child or teenager (DKOw, DKOb)".

The Decision routine 320 (FIG. 19) shows activities of the Person when he/she wants to make a decision if his/her weight, diet, and exercises are satisfactory 321. If something is wrong, the person can choose another diet plan 322 and/or change exercises 323. After a trip is accomplished and the driver has removed the key 324 from the ignition, the system keeps its own. and the weighing devices power on 325. After the driver left his/her seat 326, the system measures the driver's and passenger's car seat weights 327 and further turns it's own and the weighing device's power off 328.

The use of the on-board vehicle overweight preventive system by the driver (named in description of FIG. 2 to FIG. 26 as user, operator, person, individual or dieter) is the same as by the passenger besides the System Initialization routine (FIG. 3), Passenger Activities routine 220 (FIG. 11), and heavy traffic recognizing. The Passenger Activities routine 220 (FIG. 11) starts when the passenger activates the interrupt line 93 of the passenger activities controller 90. A passenger starts his/her activities with the on-board vehicle overweight preventive system by pushing an interrupt button on the dialog panel 92 of the passenger activities controller 90 that activates interrupt line 93 of the passenger activities controller 90. The on-board vehicle microcomputer 10 permanently monitors 221 an interrupt line of its interrupt controller 14. If the system is not busy (does not serve the driver) 222, it checks 223 a position of the switch "Separate" of the passenger activates controller 90. If this switch is turned on, the system activates 224 the passenger channel and serves the dialog with the passenger through the passenger activities controller 90. If the switch is turned off, the system 225 serves a dialog between a passenger and system through the touch-screen of the on-board vehicle microcomputer display. In this case the touch-screen of the passenger activities controller will be passive. If the system in 222 serves the driver's program, it continues to do so until it has completed serving the driver's program. According to the safety requirements of the invention, the driver is not allowed to have a dialog with the system if:

1. The gear selector is not in the Park position, or
2. There is not a situation of "Heavy traffic."

"Heavy traffic" is defined as traffic in which the vehicle is moving at a speed not higher than a certain level (see FIG. 14), for example, 10 mph. At speeds above this, operation of the system may endanger the user or other vehicle operators. At speeds below this level, it is presumed that the driver can pay attention to the system as may be required without a hazard. Of course other limitations as to when the system can be operational may also be imposed.

The driver and the passenger (or each passenger) can have respective touch screen display/input units which can be located on the dashboard, vehicle ceiling or elsewhere and positioned so that only the individual involved with use of the unit at the particular moment can see the screen which is in use. The touch screen display can also be provided on a seat structure.

I claim:

1. A method of operating an automotive vehicle having an on-board vehicle overweight and obesity preventing system including a microcomputer programmed with a weight trend analyzer, a memory and a display including touch-screen, and first and second on-board weighing apparatuses for weighing a driver or passenger other than the driver in the vehicle, said method comprising the steps of:

storing in said memory information as to a multiplicity of diets and exercise regimen suitable for a variety of different dieters;
weighing an individual comprising one of said driver and passenger with one of said first and second on-board weighing apparatuses in said vehicle;
receiving the weighed individual's weight with said microcomputer;
receiving said individual's user name and password with said microcomputer via said touch-screen display;
wherein said microcomputer further receives said individual's personal information via said touch-screen display when said individual is a new user, and stores said personal information in said memory;
determining the probability of obesity of said individual by said weight trend analyzer executed by said microcomputer;
upon forecasting obesity, prompting said individual to select an exercise plan, diet plan, and trial period;
displaying stored diet and exercise information for said individual on said touch-screen display;
reweighing said individual during said trial period using one of said on-board weighing apparatuses, and determining said individual's weight change by said weight trend analyzer;
displaying weight progress resulting from dieting for said individual on said touch-screen display request input by said individual to said microcomputer;
determining whether said individual is obese at the expiration of said trial period, and upon determination of obesity, questioning individual via said touch-screen display whether to send a warning about said obesity to individual's primary doctor; and
disabling said touch-screen display with said microcomputer from responding to the input of said driver when the speed of said vehicle is higher than a predetermined value;
wherein said vehicle speed is determined by input from a speed sensor or vehicle speedometer into said microcomputer.

2. The method defined in claim 1, further comprising the step of providing a friendly and confidential message; wherein a suggestion to start a trial weight loss plan and encouraging messages for successful obesity prevention are displayed to said individual via said touch-screen display instead of displaying said obesity warning; and
said friendly and confidential message is chosen at individual's discretion during installation of said on-board vehicle overweight and obesity preventing system.

3. The method defined in claim 1, further comprising determining weekday and weekend intake patterns by employing said weighing devices with information from a dialog with said individual or from a global position system as to names of the most popular and most used restaurants and buffets at which said individual eats at a certain time, with the names of the basic dishes and amount of calories, fat and cholesterol and automatically suggesting to said individual what kind food and how much to eat.

4. The method defined in claim 1, further comprising issuing a warning when said individual is not overweight and continuously loses weight, and his/her weight goes down to a certain level stored in said memory, and said weight trend analyzer continues to monitor weight of said individual during a certain trial period, and if said individual continues to lose weight, an on-board vehicle overweight and obesity preventing system sends a warning at individual's discretion to said individual's primary doctor.

5. The method defined in claim 1, further comprising measuring a height of a child in said vehicle by use of special markers on a rear seat of said vehicle, or by use of a supplemental cushion for car rear seat with the marks on it to measure height of the children by laying a child on the rear car seat and measure one's length or by use of a pull-out tape, and entering said height into said microcomputer via said touch-screen display.

6. The method defined in claim 1, including automatically warning at least one of the individuals by said display and a health care professional by a communication device of a developing overweight or obesity.

7. The method defined in claim 1, including providing a Comprehensive Obesity Prevention Technology (C-OPT) option, the option comprising:
automatically alerting at least one of said individuals and their health care professionals when there is a possibility that overweight or obesity may develop in a short predetermined period of time that is long enough to prevent overweight or obesity and to start treatment before the individual will become overweight or obese.

8. The method defined in claim 1, wherein said method provides measuring body parameters devices for overweight and obesity recognition that are used according to predetermined medical requirements for said individual.

9. The method defined in claim 8, wherein said body parameters include at least one of body mass index (BMI) and body fat.

10. The method defined in claim 1, including at least two weighing devices in said vehicle, including a weighing device located in a car seat of said individual in said vehicle, and an additional weighing device for the foot part of said individual that is fixed or retractable from a part of the vehicle or located in a floor mat, wherein each of said weighing device weighs a part of individual's weight.

11. The method defined in claim 10, wherein said microcomputer issues the following weighing instructions to said individual via synthesized voice:
1. when you sit down in the car seat, put your feet on a weighing device near your feet;
2. keep your hands on your knees, don't touch anything in the car by hand and don't push the seat back against your back for a few seconds; and
3. buckle the seat belt.

12. The method defined in claim 10, wherein weighing said individual comprises determining a true weight of said individual by processing acquired data over an interval;
wherein said interval begins when said individual engages said on-board weighing apparatuses and ends when said individual engages a seat belt;
wherein said true weights reflect a measurement during which hands of the individual are not resting on a surface.

13. The method defined in claim 10, wherein said weighing device for the foot part of said individual that is fixed or retractable from a part of the vehicle or located in a floor mat contains information to sense that said individual changed shoes when a foot portion of weight of said individual is analyzed relative to the weight of a car seat portion of said individual's body.

14. The method defined in claim 10, wherein said vehicle includes an air bag safety system at a front of the vehicle, and wherein said additional weighing device for the foot part of said individual is fixed or retractable from a part of the vehicle or located in a floor mat, signals whether the passenger is facing front, thereby preventing triggering the air bag against a rear facing front passenger.

15. The method defined in claim 10, wherein said driver is weighed while said vehicle is running, using said on-board weighing apparatus comprising a device located in a car seat of said driver in said vehicle, and said additional weighing device comprises two additional weighing devices;
wherein the first of said additional weighing devices is located on the vehicle floor, footrest, in a floor mat, or in other suitable location; and
the second of said additional weighing devices is fixed on the gas pedal;
wherein one foot of the driver will push the gas pedal via the second additional weighing device and the other foot of said driver will be on the first of said additional weighing devices.

16. The method defined in claim 1, further comprising checking of a state of individual seat belt and existence of an individual's feet on a weighing device when said individual is sitting down in an individual car seat.

17. The method defined in claim 16, wherein said method provides measuring tension in said seat belt during a period of time from the moment when said individual sits in the vehicle to a moment in time when a signal appears that a seat belt is buckled.

18. The method defined in claim 1, wherein said method, after diagnosing possible overweight or obesity that may occur in a short predetermined period of time, will suggest that the individual may begin an exercise program for a trial period calculated by said microcomputer depending on age and an overweight or obesity level of said individual, provide lifestyle recommendations of a medical authority, and positively reinforce healthy weight trends during said trial period.

19. The method defined in claim 18, wherein said overweight and obesity preventing system at the discretion of a manufacturer, provides recommendation messages from medical and nutrition authorities to said individual.

20. The method defined in claim 1, further comprising creating a database of said in said memory;
wherein said database includes personal data transmitted to said microcomputer of said individual or medical facility depending on the age of said individual.

21. The method defined in claim 1, including storing a vehicle change procedure in said memory of said on-board vehicle microcomputer, to keep or remove personal data of said individual that employs said on-board vehicle overweight and obesity preventing system in case of selling said vehicle or buying a new vehicle.

22. The method defined in claim 1, wherein said method further prevents future overweight and obesity by determining by said weight trend analyzer said individual's weight progress and predicting overweight or obesity of at least one of a driver and passengers in said vehicle, and by selecting from said on-board vehicle overweight and obesity preventing system's memory at least one of lifestyle recommendations, exercises, and diets, included by permission of the medical and nutrition authorities that are interested in the overweight or obese individuals in the early stages of illness.

23. The method defined in claim 1, wherein said method determines by said weight trend analyzer said individual's weight change from a previous measurement exceeding a certain magnitude, ascertains whether there has been a change in clothing, footwear, or extraneous weight since the previous measurement processing a correlation of the separate measurements of the body and foot parts of said individual weight and by a dialogue with said individual and checking a temperature sensor connected to said microcomputer and memorizing its output for creating data that correlates clothing or footwear to outside vehicle temperature.

* * * * *